(12) United States Patent
Strommer et al.

(10) Patent No.: US 7,386,339 B2
(45) Date of Patent: Jun. 10, 2008

(54) MEDICAL IMAGING AND NAVIGATION SYSTEM

(75) Inventors: Gera M. Strommer, Haifa (IL); Uzi Eicher, Haifa (IL)

(73) Assignee: Mediguide Ltd., Haifa (IL)

(*) Notice: Subject to any disclaimer, the term of this patent is extended or adjusted under 35 U.S.C. 154(b) by 787 days.

(21) Appl. No.: 09/782,528

(22) Filed: Feb. 13, 2001

(65) Prior Publication Data

US 2001/0031919 A1 Oct. 18, 2001

Related U.S. Application Data

(63) Continuation-in-part of application No. 09/314,474, filed on May 18, 1999, now Pat. No. 6,233,476.

(51) Int. Cl.
*A61B 5/05* (2006.01)

(52) U.S. Cl. .............. 600/424; 600/428; 600/429

(58) Field of Classification Search .............. 600/407, 600/425, 426, 437–439, 413, 417, 427–429; 606/130; 378/20, 205, 69
See application file for complete search history.

(56) References Cited

U.S. PATENT DOCUMENTS

| | | | |
|---|---|---|---|
| 3,974,826 A | 8/1976 | Eggleton et al. ............. 128/2 V |
| 3,990,296 A | 11/1976 | Erikson ................... 73/67.5 H |
| 4,737,794 A | 4/1988 | Jones .......................... 342/448 |
| 5,016,642 A | 5/1991 | Dukes et al. ............... 128/696 |
| 5,152,290 A | 10/1992 | Freeland ................ 128/660.07 |
| 5,159,931 A | 11/1992 | Pini ........................ 128/660.07 |
| 5,398,691 A | 3/1995 | Martin et al. .......... 128/662.06 |
| 5,453,686 A | 9/1995 | Anderson .............. 324/207.17 |
| 5,529,070 A | 6/1996 | Augustine et al. ..... 128/660.07 |
| 5,577,502 A | 11/1996 | Darrow et al. |
| 5,588,432 A | 12/1996 | Crowley ................ 128/660.07 |
| 5,622,174 A | 4/1997 | Yamazaki |
| 5,669,385 A | 9/1997 | Pesque et al. |
| 5,690,113 A | 11/1997 | Sliawa, Jr. et al. ..... 128/660.07 |
| 5,744,953 A | 4/1998 | Hansen .................. 324/207.17 |
| 5,787,889 A | 8/1998 | Edwards et al. ........ 128/660.07 |
| 5,806,521 A | 9/1998 | Morimoto et al. ..... 128/661.01 |
| 5,830,145 A | 11/1998 | Tenhoff ...................... 600/463 |
| 5,830,222 A | 11/1998 | Makower |
| 5,846,200 A | 12/1998 | Schwartz .................... 600/443 |
| 5,899,860 A | 5/1999 | Pfeiffer et al. .............. 600/424 |
| 5,913,820 A | 6/1999 | Bladen et al. .............. 600/407 |
| 5,924,989 A | 7/1999 | Polz .......................... 600/443 |
| 5,928,248 A | 7/1999 | Acker |

(Continued)

*Primary Examiner*—Brian L. Casler
*Assistant Examiner*—Baisakhi Roy
(74) *Attorney, Agent, or Firm*—Darby & Darby P.C.

(57) ABSTRACT

Medical imaging and navigation system including a processor, a display unit, a database, a medical positioning system (MPS), a two-dimensional imaging system, an inspected organ monitor interface, and a superimposing processor, the MPS including a transducer MPS sensor and a surgical tool MPS sensor, the two-dimensional imaging system including an imaging transducer, the processor being connected to the display unit, to the database, to the MPS, to the two-dimensional imaging system, to the inspected organ monitor interface, and to the superimposing processor, the inspected organ monitor interface being connected to an organ monitor, the surgical tool MPS sensor being firmly attached to a surgical tool, the transducer MPS sensor being firmly attached to the imaging transducer, the organ monitor monitoring an organ timing signal associated with an inspected organ.

102 Claims, 16 Drawing Sheets

U.S. PATENT DOCUMENTS

| | | | |
|---|---|---|---|
| 5,935,075 A | 8/1999 | Casscells | 600/474 |
| 5,938,606 A | 8/1999 | Bonnefous et al. | |
| 5,949,491 A | 9/1999 | Callahan et al. | 348/442 |
| 5,955,879 A | 9/1999 | Durdle et al. | 324/207.17 |
| 5,957,844 A | 9/1999 | Dekel et al. | 600/439 |
| 5,967,980 A | 10/1999 | Ferre et al. | 600/424 |
| 5,976,088 A | 11/1999 | Urbano et al. | 600/443 |
| 5,993,390 A | 11/1999 | Savord et al. | 600/437 |
| 5,994,690 A | 11/1999 | Kulharni et al. | 250/216 |
| 6,006,126 A * | 12/1999 | Cosman | 600/426 |
| 6,035,856 A | 3/2000 | LaFontaine et al. | |
| 6,047,080 A | 4/2000 | Chen et al. | |
| 6,134,003 A | 10/2000 | Tearney et al. | 356/345 |
| 6,148,095 A | 11/2000 | Prause et al. | |
| 6,169,917 B1 | 1/2001 | Masotti et al. | |
| 6,175,669 B1 | 1/2001 | Colston et al. | 385/12 |
| 6,216,029 B1 | 4/2001 | Paltieli | 600/427 |
| 6,246,898 B1 | 6/2001 | Vesely et al. | |
| 6,261,247 B1 * | 7/2001 | Ishikawa et al. | 600/587 |
| 6,317,621 B1 | 11/2001 | Graumann et al. | |
| 6,321,109 B2 | 11/2001 | Ben-Haim et al. | |
| 6,385,476 B1 | 5/2002 | Osadchy et al. | |
| 6,390,982 B1 | 5/2002 | Bova et al. | 600/443 |
| 6,405,072 B1 | 6/2002 | Cosman | 600/426 |
| 6,423,009 B1 | 7/2002 | Downey et al. | |
| 6,470,207 B1 * | 10/2002 | Simon et al. | 600/426 |
| 6,501,981 B1 * | 12/2002 | Schweikard et al. | 600/427 |
| 6,546,271 B1 | 4/2003 | Reisfeld | |
| 6,556,695 B1 | 4/2003 | Packer et al. | |
| 6,587,707 B2 | 7/2003 | Nehrke et al. | |
| 6,626,902 B1 | 9/2003 | Kucharczyk et al. | |
| 7,235,084 B2 | 6/2007 | Skakoon et al. | |
| 2002/0049375 A1 | 4/2002 | Strommer et al. | |
| 2002/0193686 A1 | 12/2002 | Gilboa | |
| 2004/0097804 A1 | 5/2004 | Sobe | |
| 2006/0058647 A1 | 3/2006 | Strommer et al. | |
| 2006/0064006 A1 | 3/2006 | Strommer et al. | |

* cited by examiner

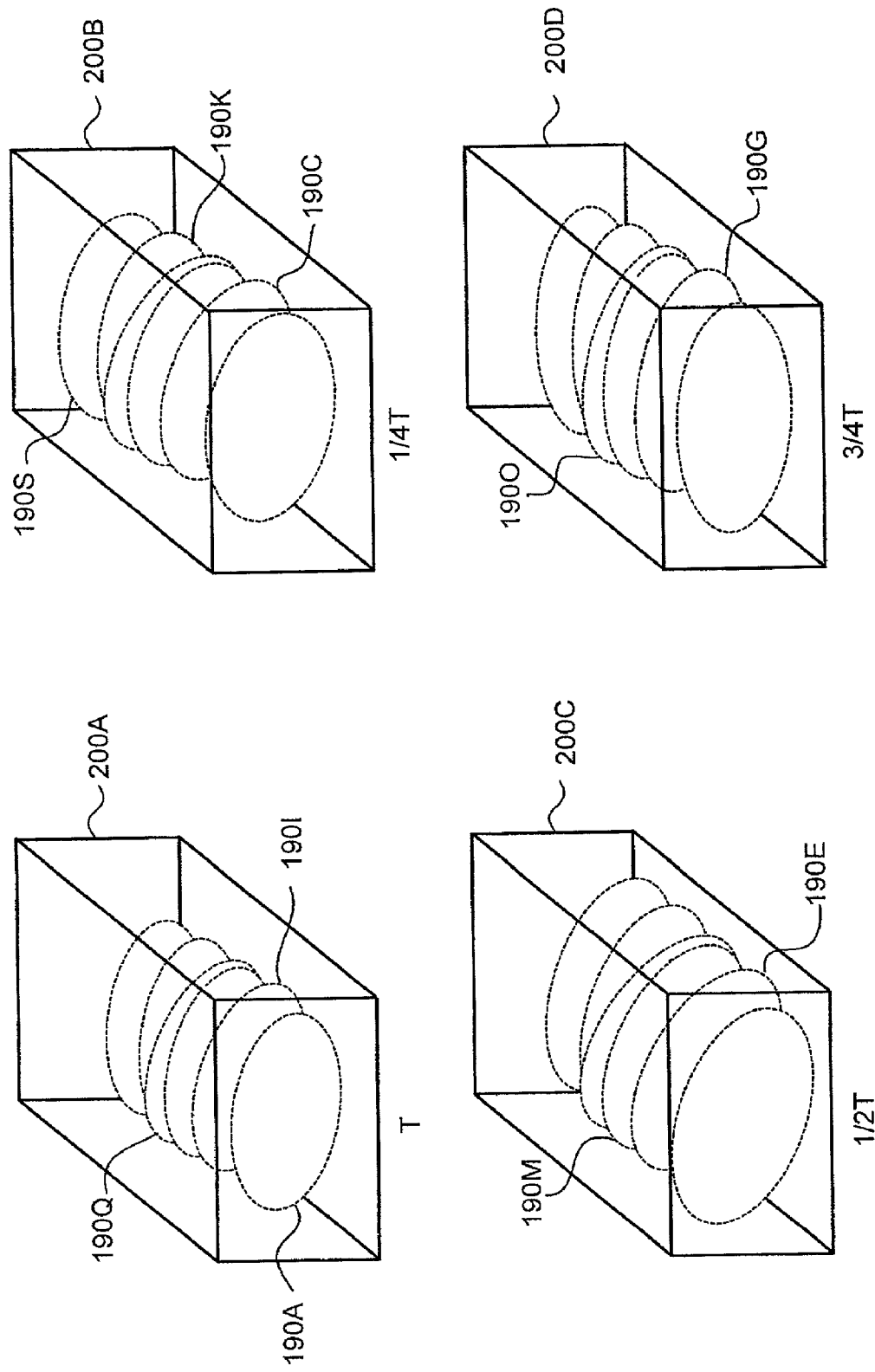

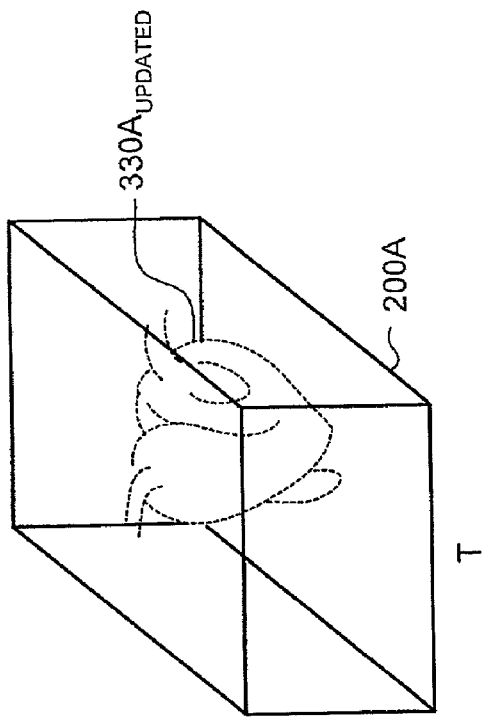
FIG. 5C
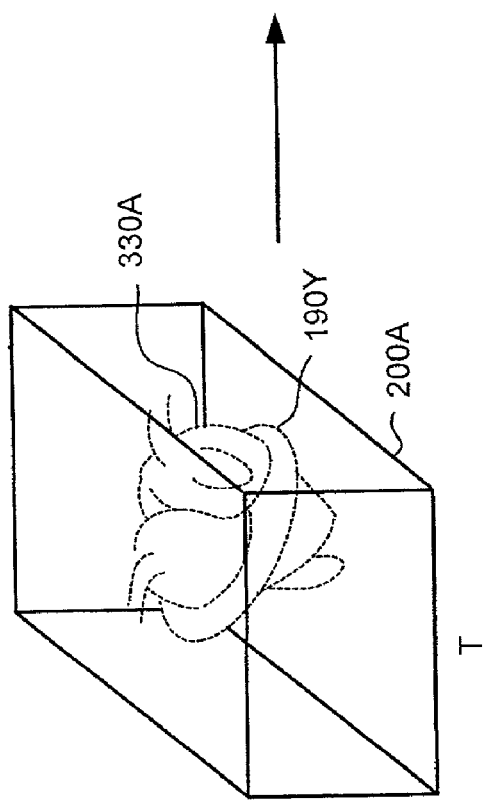
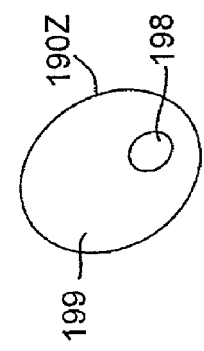
FIG. 5D

MEDICAL IMAGING AND NAVIGATION SYSTEM

CROSS REFERENCE INFORMATION

This application is a Continuation-in-Part of application Ser. No. 09/314,474, filed May 18, 1999, now U.S. Pat. No. 6,233,476.

FIELD OF THE INVENTION

The present invention relates to medical diagnostic and surgery systems and methods in general, and to methods and systems for three-dimensional medical imaging and navigation, in particular.

BACKGROUND OF THE INVENTION

Methods and systems for acquiring and presenting two-dimensional and three-dimensional images are known in an art. Three-dimensional imaging enhances modern diagnostics, therapy and surgery procedures.

A two-dimensional imaging system processes and represents two-dimensional internal body slices in static or in dynamic form on a display. A conventional two-dimensional ultrasound imaging system includes an ultrasound transducer, an image capturing module and an image-processing unit.

The ultrasound transducer is placed in close proximity to the tissue to be examined. The ultrasound transducer converts an electrical signal to ultrasonic waves and directs the waves toward the examined tissue. The ultrasonic waves are in part absorbed, dispersed, refracted and reflected. The ultrasound transducer detects the ultrasonic reflections. The ultrasound transducer converts the reflected ultrasonic waves to an electrical signal and provides it to the image-processing unit.

The image-processing unit processes the received electrical signal, thereby producing a plurality of two-dimensional images of slices of the inspected tissue. The image-capturing module captures each two-dimensional image and can provide each of them to a display or a printer.

U.S. Pat. No. 5,152,290 to Freeland, entitled "Method for recording ultrasound images to diagnose heart and coronary artery disease" is directed to a method for capturing and displaying two-dimensional ultrasound images of the heart for diagnosing heart disease, such as coronary artery disease. The method disclosed by Freeland includes the steps of detecting an electrocardiogram (ECG) signal after peak exercise, detecting the two-dimensional images of the heart, storing selected images, each with the ECG reading at the time that the image was taken and displaying a quad-image group. The system detects and records a two-dimensional image sequence continuously at a rate of at least eight images per heartbeat.

U.S. Pat. No. 5,690,113, issued to Sliwa, Jr. et al., entitled "Method and apparatus for two-dimensional ultrasonic imaging" is directed to a method and apparatus for generating a two-dimensional ultrasonic image using a hand-held single element transducer probe, having a fixed scan-line. The system provides displaying two-dimensional ultrasonic images of the body of a patient. This system detects two-dimensional ultrasonic images, and determines the spatial location and orientation of the ultrasound transducer, at the same time. The system includes a probe with an ultrasound transducer, capable of imaging a single scan-line and a means for tracking the spatial location and orientation of the ultrasound transducer. The scan-line is fixed in an orientation and spatial position relative to the movable transducer. The system further includes a computing means, which computes the spatial location and the orientation of each scan-line as the transducer is moved. Thereby, the scan-lines are presented as a complete image. Alternatively, an electromagnetic transmitter and receiving sensor determine the spatial orientation and position of each scan-line in free space.

A typical three-dimensional ultrasound imaging system includes a conventional two-dimensional ultrasound imaging system, a location and orientation detection system, an image processing system and a displaying system. Such systems provide three-dimensional imaging of internal organs such as the liver, kidneys, gallbladder, breast, eyes, brain, and the like.

The location and orientation detection system provides the location and orientation of ultrasound transducer. The location and orientation of each of the captured two-dimensional images are determined from the location and orientation of the transducer.

The image processing system reconstructs a three-dimensional image of the inspected organ, by processing the captured two-dimensional images, each according to the location and orientation thereof. Finally, the displaying system displays the received three-dimensional image of the inspected organ.

U.S. Pat. No. 5,787,889 issued to Edwards et al., and entitled "Ultrasound imaging with real time 3D image reconstruction and visualization" is directed to generation and visualization of three-dimensional ultrasound images. The method disclosed by Edwards includes the following steps: acquiring data, reconstructing a volume, and visualizing an image. The system provides for achieving and visualizing three-dimensional ultrasound images with a two-dimensional ultrasound medical imaging system included therein. An operator can perform various visualization tasks on the reconstructed three-dimensional image, such as rotating the image in different viewing angles and plans.

Another type of three-dimensional imaging system, which is known in the art, is operative to produce a motion picture of the heart or the lungs. This system includes a conventional two-dimensional ultrasound imaging system, an ECG monitor, a location and orientation detection system, an image processor and a display system. The ECG monitor detects the timing signal of the heart. The ECG timing signal is used to synchronize or trigger the recording of the two-dimensional images representative of selected points in the ECG timing signal. The ultrasound transducer detects two-dimensional ultrasound images of the heart at any given moment (e.g., at a selected point of time on ECG timing signal). Each two-dimensional image represents a specific slice of the heart according to the specific activity-state thereof. The location and orientation of each of the two-dimensional images are directly determined from the location and orientation of the transducer.

The image processor reconstructs a three-dimensional image of the heart from captured two-dimensional images having the same activity-state. Finally, the display system displays a sequence of the reconstructed images, thereby presenting a three-dimensional motion picture of the heart.

U.S. Pat. No. 5,924,989 issued to Polz, and entitled "Method and device for capturing diagnostically acceptable three-dimensional ultrasound image data records", is directed to a method and a system for generating a three-dimensional image sequence of the heart. This system includes a three-dimensional ultrasound imaging system, combined with an echocardiograph. The system detects two-dimensional ultrasound images and stores each of them together with the location and orientation thereof and with the organ cycle location as provided by the echocardiogram, at the time that the image was acquired.

Utilizing a special algorithm, the system reconstructs a three-dimensional image from all of the two-dimensional images having the same organ cycle location, and displays a sequence of the reconstructed three-dimensional images.

SUMMARY OF THE PRESENT INVENTION

It is an object of the present invention to provide a novel method and system for medical in-vivo invasive probing. In accordance with the present invention, there is thus provided a medical imaging and navigation system. The system includes a processor, a display unit, a database, a medical positioning system (MPS), a two-dimensional imaging system, an inspected organ monitor interface, and a superimposing processor.

The MPS includes a transducer MPS sensor and a surgical tool MPS sensor. The two-dimensional imaging system includes an imaging transducer. The processor is connected to the display unit, the database, the MPS, the two-dimensional imaging system, the inspected organ monitor interface, and to the superimposing processor. The inspected organ monitor interface is further connected to an organ monitor. The surgical tool MPS sensor is firmly attached to a surgical tool. The transducer MPS sensor is firmly attached to the imaging transducer. The organ monitor monitors an organ timing signal associated with an inspected organ. The system reconstructs a plurality of three-dimensional images from a plurality of detected two-dimensional images, according to the respective location and orientation of each two-dimensional image and its position within the inspected organ timing signal. Since the all of the MPS sensors belong to the same MPS system, the system provides the location and orientation of the surgical tool, within the same coordinate system of the detected two-dimensional images.

In accordance with another aspect of the present invention, there is thus provided a medical imaging and navigation system. The system includes a processor, a display unit, a database, an MPS, an inspected organ monitor interface and a superimposing processor. The processor is connected to the display unit, the database, the MPS, the inspected organ monitor interface and to the superimposing processor. The inspected organ monitor interface is connected to an organ monitor. The MPS includes a surgical tool MPS sensor being firmly attached to a surgical tool. The organ monitor monitors an organ timing signal associated with an inspected organ. This system is adapted to operate on pre-stored images.

In accordance with a further aspect of the present invention, there is thus provided a method for displaying an image sequence of a moving inspected organ. The method includes the steps of detecting an organ timing signal of the inspected organ, detecting a plurality of two-dimensional images of the inspected organ using an image detector, and detecting the location and orientation of the image detector. The method further includes the steps of associating each of the two-dimensional images with the image detector location and orientation and with the detected organ timing signal, and reconstructing a plurality of three-dimensional images from the two-dimensional images. The method further includes the steps of selecting one of the three-dimensional images according to a real-time reading of the organ timing signal, and displaying the selected three-dimensional image.

In accordance with another aspect of the present invention, there is thus provided a method for displaying an image sequence of a moving inspected organ. The method includes the steps of detecting an organ timing signal of the inspected organ, and selecting one of a previously stored three-dimensional images according to a real-time reading of the organ timing signal. The method further includes the steps of detecting the location and orientation of a surgical tool, superimposing a representation of the surgical tool onto the selected three-dimensional image, and displaying the superimposed three-dimensional image.

In accordance with a further aspect of the present invention, there is thus provided a method for displaying an image sequence of a moving inspected organ. The method includes the steps of detecting an organ timing signal of the inspected organ, detecting the location and orientation of a point of view of a user and selecting one of a previously stored three-dimensional images according to a real-time reading of the organ timing signal. The method further includes the steps of rendering the selected three-dimensional image according to the detected location and orientation of the point of view and displaying the selected three-dimensional image.

In accordance with another aspect of the present invention, there is thus provided a method for displaying an image sequence of a moving inspected organ. Each image in the image sequence is associated with the location and orientation of the image within a predetermined coordinate system. The method includes the steps of detecting an organ timing signal of the inspected organ, selecting one of a previously stored two-dimensional images according to a real-time reading of the organ timing signal and displaying the selected two-dimensional image. This system is adapted for a two-dimensional imaging and displaying environment.

BRIEF DESCRIPTION OF THE DRAWINGS

The present invention will be understood and appreciated more fully from the following detailed description taken in conjunction with the drawings in which:

FIG. 5A is a schematic illustration of a plurality of three-dimensional volumes, according to another preferred embodiment of the present invention;

FIG. 5C is a schematic illustration of a selected three-dimensional volume of FIG. 5A, going through a procedure of image updating;

FIG. 5D is a schematic illustration of a two-dimensional image which includes foreign object information;

DETAILED DESCRIPTION OF PREFERRED EMBODIMENTS

Figure 1:
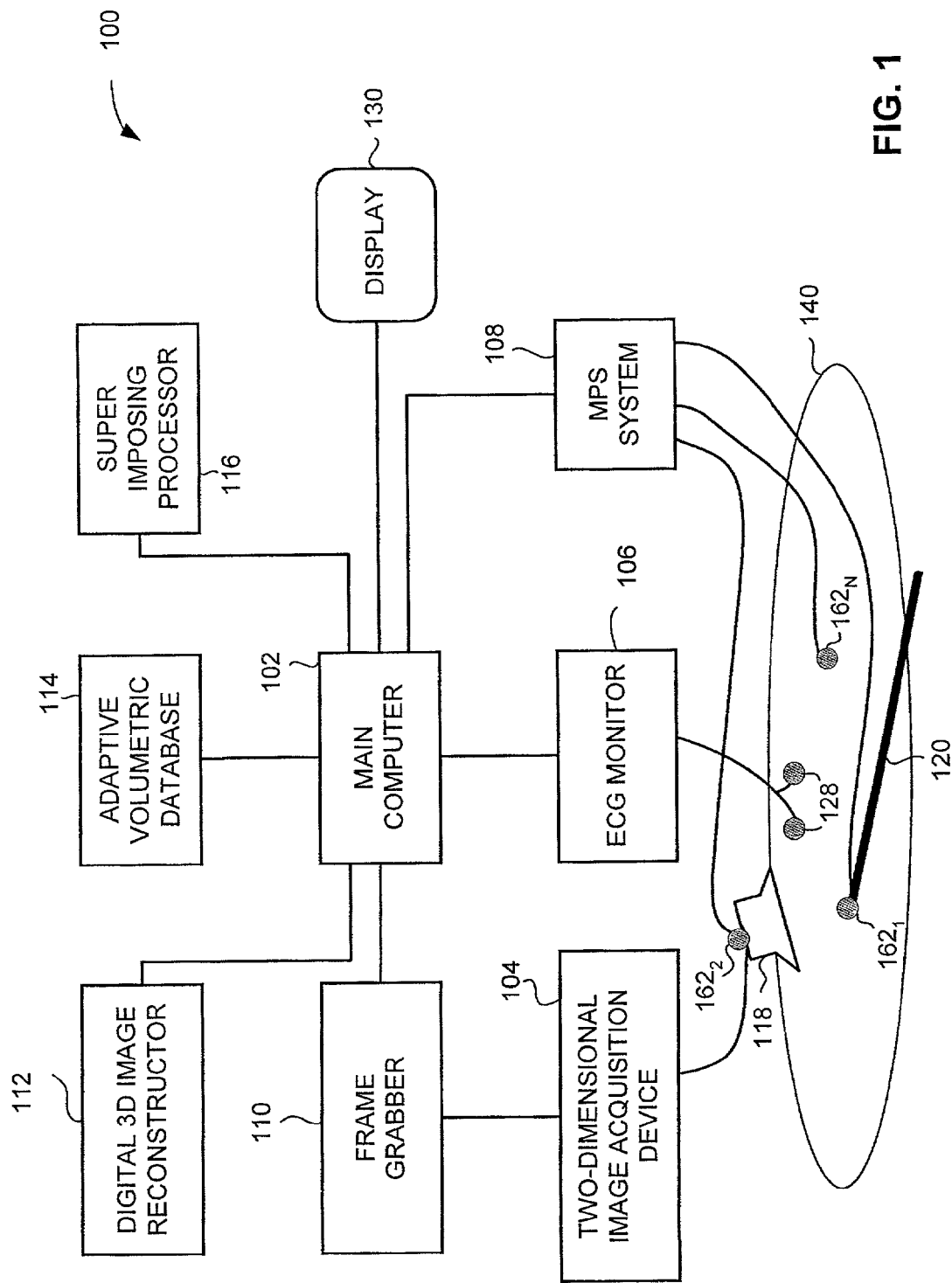
FIG. 1 is a schematic illustration of a multi functional three-dimensional imaging system, constructed and operative in accordance with a preferred embodiment of the present invention.

The present invention overcomes the disadvantages of the prior art by providing methods and systems for constructing and displaying three-dimensional images of moving organs, synchronously with the movement of these organs and synchronously with an invasive tool, such as a catheter. According to a preferred embodiment, the three-dimensional images and the presentation of the invasive tool, all reside within a single coordinate system, and no registration of a plurality of coordinate systems is required.

According to one aspect of the invention there is provided a pseudo real time imaging system, for minimal invasive surgery. This system includes a two-dimensional image acquisition system, a medical positioning system (MPS) which is basically a location and orientation detection system, a specific organ monitor and an image processing system. The location and orientation detection system includes at least three sensors. The first sensor is mounted on the image detector of the two-dimensional image acquisition system. The second sensor is mounted on the minimal invasive surgery tool. The third sensor is attached to the body of the patient for reference. Attaching the third sensor is the body of the patient during all of the steps of the method of the disclosed technique, assures that both the sensor of the image detector and the sensor of the surgical tool, as well as additional sensors which are attached to further modules of the system of the invention, remain in a single coordinate system at all times.

The system acquires two-dimensional images at a rate, faster than the organ cycle frequency, and preferably equal to the organ cycle frequency multiplied by a natural number. The system records each two-dimensional image, acquired by the image detector, in association with the detected location and orientation thereof, and with the organ timing signal reading, as detected by the organ monitor. It is noted that the system operates under the assumption that the detected organ is characterized by a cyclic behavior, and that a reading in one cycle is likely to be detected in subsequent cycles.

The imaging system reconstructs a three-dimensional image from all of the recorded two-dimensional images, which have the same organ timing signal reading (from different cycles). When the reconstructed three-dimensional images include sufficient information, the system displays a sequence of these three-dimensional images, synchronized with a real-time reading of the organ timing signal, thereby providing a real-time visualization of the inspected organ. At the same time, the system continues to acquire additional two-dimensional images and to update and elaborate the existing three-dimensional image. Hence, the quality of the displayed sequence of three-dimensional images, constantly improves.

At this point, the physician can insert a minimal invasive surgical tool into the body of the patient. The system detects the location and orientation of the MPS detector mounted on the surgical tool and super-imposes a representation thereof, on the currently displayed three-dimensional image.

The system detects movements of the patient using the MPS detector, which is attached to the patient. These movements shift the coordinate system of the detected organ relative to the coordinate system in which the two-dimensional images were acquired and the three-dimensional images are reconstructed. The system utilizes the patient MPS reading both for placing all the acquired two-dimensional images in a moving coordinate system defined by the location of the inspected organ, and for placing the location and orientation of the surgical tool, in that same moving coordinate system.

According to another aspect of the invention, by removing the surgical tool, the system can be used merely as a pseudo real-time imaging system, used for diagnostic purposes.

According to a further aspect of the invention, the system displays the three-dimensional image sequence, using semi transparent stereoscopic goggles, which have an MPS sensor attached thereto. The system uses the goggles MPS sensor to place the location and orientation of the goggles, within the coordinate system of the patient. Accordingly, the system produces a visualization of the three-dimensional image sequence, which is perceived by the physician, as being located at the same place of the organ.

The following is an example of a system and method for image acquisition, playback and minimal invasive surgery, where the inspected organ is a heart.

Reference is now made to FIG. 1, which is a schematic illustration of a multi functional three-dimensional imaging system, generally referenced 100, constructed and operative in accordance with a preferred embodiment of the present invention. In the example set forth in FIG. 1, system 100 is adapted for producing a three-dimensional image sequence of the heart and playing it in real time synchronicity, with the motion of the heart.

Three-dimensional imaging system 100 includes, a main computer 102, a two-dimensional image acquisition device 104, an ECG monitor 106, a medical positioning system (MPS) 108, a frame grabber 110, a digital three-dimensional image reconstructor (D3DR) 112, an adaptive volumetric database (AVDB) 114, a superimposing processor 116, a surgical tool 120, a plurality of MPS sensors $162_1$, $162_2$ and $162_N$, and a display 130.

Two-dimensional image acquisition device 104 provides a two-dimensional image of an area within the body of the patient. Two-dimensional image acquisition device 104 can be of any type known in the art, such as ultra-sound, inner-vascular ultra-sound, X-ray, computerized tomography, nuclear magnetic resonance, positron-emission tomography, single-photon-emission tomography, and the like.

Two-dimensional image acquisition device 104 includes an image transducer 118. ECG-monitor continuously detects an electrical timing signal of the heart during inspection or surgery procedure, by employing a plurality of ECG-electrodes 128.

Main computer 102 is connected to ECG monitor 106, MPS system 108, frame grabber 110, D3DR 112, superimposing processor 116, AVDB 114 and to display 130. Two-dimensional image acquisition device 104 is connected to frame grabber 110. MPS system 108 includes an MPS transmitter (not shown) and MPS sensors $162_1$, $162_2$ and $162_N$.

Figure 2A:
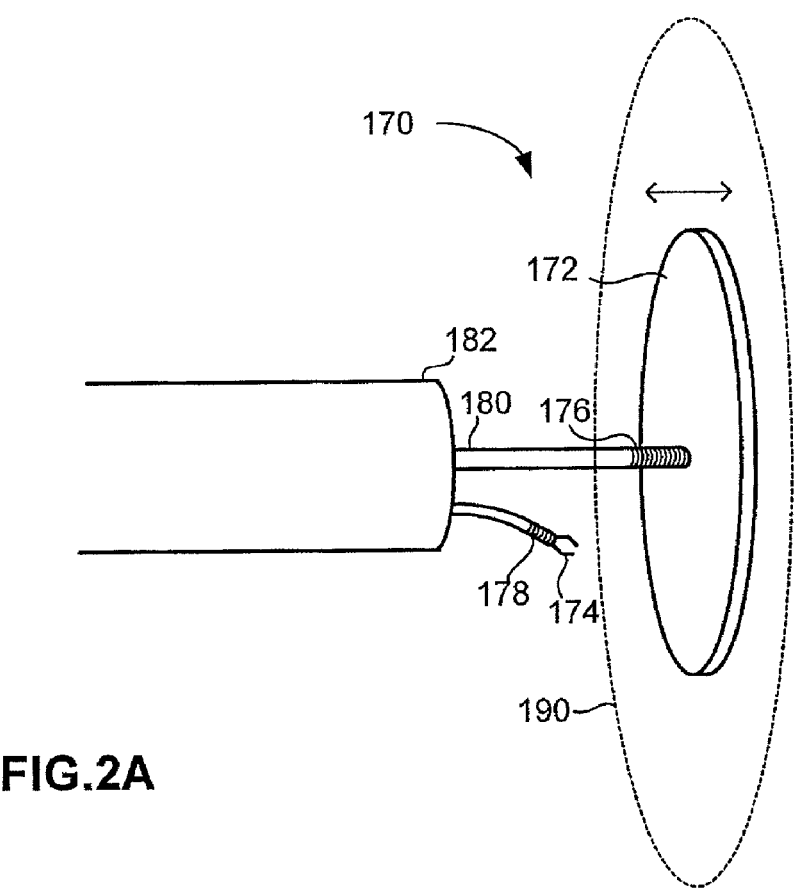
FIG. 2A is an illustration in perspective of an inner-body radial ultrasound imaging system, constructed and operative in accordance with another preferred embodiment of the present invention.
Figure 2B:
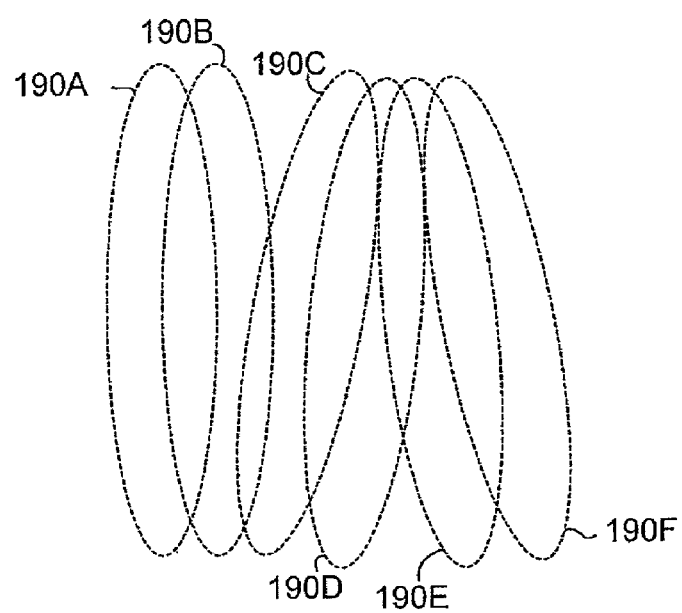
FIG. 2B is an illustration in perspective of a plurality of radial two-dimensional images of the walls of an inspected vessel.
Figure 2C:
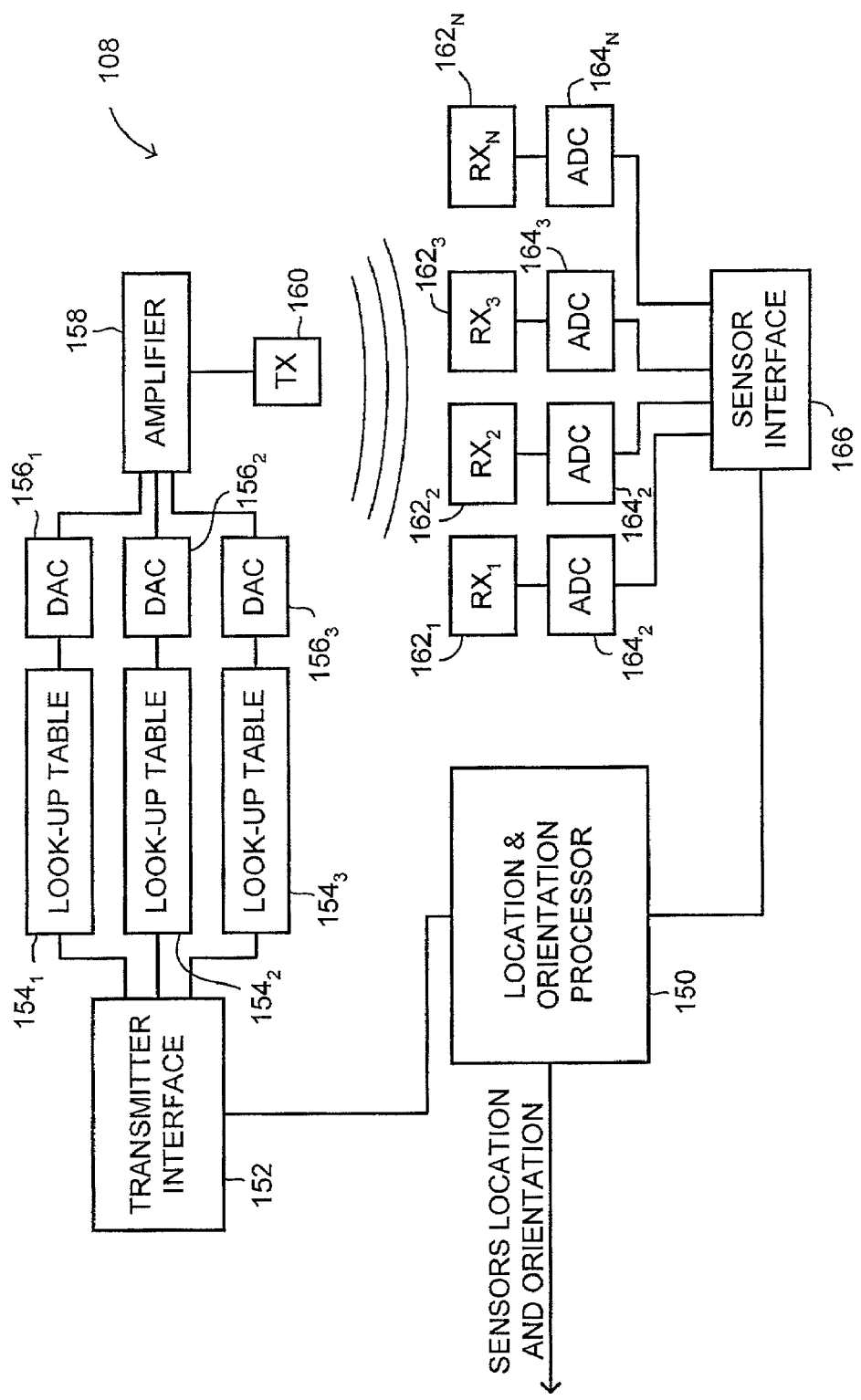
FIG. 2C is a schematic illustration in detail of the MPS system of FIG. 1, constructed and operative in accordance with a further preferred embodiment of the present invention.

Reference is further made to FIG. 2C, which is a schematic illustration in detail of MPS system 108, constructed and operative in accordance with another preferred embodiment of the present invention. MPS system 108 includes a location and orientation processor 150, a transmitter interface 152, a plurality of look-up table units $154_1$, $154_2$ and $154_3$, a plurality of digital to analog converters (DAC) $156_1$, $156_2$ and $156_3$, an amplifier 158, a transmitter 160, a plurality of MPS sensors $162_1$, $162_2$, $162_3$ and $162_N$, a plurality of analog to digital converters (ADC) $164_1$, $164_2$, $164_3$ and $164_N$ and a sensor interface 166.

Transmitter interface 152 is connected to location and orientation processor 150 and to look-up table units $154_1$, $154_2$ and $154_3$. DAC units $156_1$, $156_2$ and $156_3$ are connected to a respective one of look-up table units $154_1$, $154_2$ and $154_3$ and to amplifier 158. Amplifier 158 is further connected to transmitter 160. Transmitter 160 is also marked TX. MPS sensors $162_1$, $162_2$, $162_3$ and $162_N$ are further marked $RX_1$, $RX_2$, $RX_3$ and $RX_N$, respectively.

Analog to digital converters (ADC) $164_1$, $164_2$, $164_3$ and $164_N$ are respectively connected to sensors $162_1$, $162_2$, $162_3$ and $162_N$ and to sensor interface 166. Sensor interface 166 is further connected to location and orientation processor 150.

Each of look-up table units $154_1$, $154_2$ and $154_3$ produces a cyclic sequence of numbers and provides it to the respective DAC unit $156_1$, $156_2$ and $156_3$, which in turn translates it to a respective analog signal. Each of the analog signals is respective of a different spatial axis. In the present example, look-up table $154_1$ and DAC unit $156_1$ produce a signal for the X axis, look-up table $154_2$ and DAC unit $156_2$ produce a signal for the Y axis and look-up table $154_3$ and DAC unit $156_3$ produce a signal for the Z axis.

DAC units $156_1$, $156_2$ and $156_3$ provide their respective analog signals to amplifier 158, which amplifies and provides the amplified signals to transmitter 160. Transmitter 160 provides a multiple axis electromagnetic field, which can be detected by MPS sensors $162_1$, $162_2$, $162_3$ and $162_N$. Each of MPS sensors $162_1$, $162_2$, $162_3$ and $162_N$ detects an electromagnetic field, produces a respective electrical analog signal and provides it to the respective ADC unit $164_1$, $164_2$, $164_3$ and $164_N$ connected thereto. Each of the ADC units $164_1$, $164_2$, $164_3$ and $164_N$ digitizes the analog signal fed thereto, converts it to a sequence of numbers and provides it to sensor interface 166, which in turn provides it to location and orientation processor 150.

Location and orientation processor 150 analyzes the received sequences of numbers, thereby determining the location and orientation of each of the MPS sensors $162_1$, $162_2$, $162_3$ and $162_N$. Location and orientation processor 150 further determines distortion events and updates look-up tables $154_1$, $154_2$ and $154_3$, accordingly.

Referring back to FIG. 1, image transducer 118 detects a plurality of two-dimensional images, each representing a slice of the inspected organ (i.e., the heart). Each of these two-dimensional images has a different spatial location and orientation.

Frame grabber 110 grabs each detected two-dimensional image and provides it to main computer 102. MPS system 108 receives and processes data related to the location and orientation of surgical tool 120 via MPS sensor $162_1$ and processes data related to the location and orientation of image transducer 118 via MPS sensor $162_2$.

MPS system 108 further receives and processes data related to the location and orientation of the body of a patient, via MPS sensor $162_N$. It is noted that MPS sensor $162_N$ is used as reference in case the patient Moves. MPS sensor $162_N$ is generally attached to an inspected area of a patient body (reference 140). It is noted that MPS system 108 can include additional MPS sensors, to be used as further references, thereby enhancing the performance of system 100. it is noted however that other methods for assigning a reference point can be used such as initial referencing between all of the MPS sensors and strapping the patient during the entire procedure, analyzing the acquired images and identifying a recurring visual point or section therein for each of the MPS sensors other than the one for the transducer, and the like.

MPS system 108 produces predetermined electromagnetic fields using the MPS transmitter. Each of the MPS sensors $162_1$, $162_2$ and $162_N$ includes electromagnetic field detection elements, such as coils, for detecting the electromagnetic fields produced by MPS system 108.

MPS system 108 processes the detected electromagnetic fields and provides an indication of the three-dimensional location and orientation of MPS sensors $162_1$, $162_2$ and $162_N$. Hence, MPS system 108 is operative to determine the location and orientation of image transducer 118, surgical tool 120 and a selected point on the body of the patient.

The location and orientation of each of the captured two-dimensional images are directly derived from the location and orientation of image transducer 118. Hence, by determining the location and orientation of MPS sensor $162_2$, MPS system 108 can determine the location and orientation of each of the two-dimensional images captured by image transducer 118.

ECG monitor 106 obtains and represents an electrical timing signal (ECG—electrocardiogram) of the inspected heart. It is noted that ECG is a heart timing signal, which includes EGG cycles and represents the propagation of electrical currents through specific regions of the heart. The duration of an EGG cycle (or cardiac cycle) is defined as the time between two subsequent heart contractions. ECG is detected using at least two ECG-electrodes, which are placed on selected areas of the body of the patient (e.g., the arms, legs, chest, abdomen, and the like).

ECG-electrodes 128 continuously obtain an electrical signal from the heart and provide this signal to ECG monitor 106. ECG monitor 106 amplifies the received electrical signal, produces a graphic line tracing the electrical activity of the heart, as a function of the time, and provides this data in digital format to main computer 102.

Main computer 102 receives each of the two-dimensional images, the respective three-dimensional location and orientation of that specific two-dimensional image and the organ timing signal of the heart at the time the image was captured. Main computer 102 can further receive the three-dimensional location and orientation of surgical tool 120.

Main computer 102 associates each detected two-dimensional image, with the location and orientation information and the heart-timing signal.

When the surgical tool 120 is located within the inspected organ, a two-dimensional image can include a sliced representation of a portion thereof. Main computer 102 receives the location and orientation of MPS sensor $162_1$, which is attached to the surgical tool and can extrapolate the location and orientation of a larger portion of the surgical tool, in case that portion of the surgical tool is substantially rigid. Hence, main computer 102 can determine if that portion of surgical tool 120 is located within an area of the acquired two-dimensional image. Main computer 102 can discard this area, while updating the three-dimensional image, which the two-dimensional image belongs to.

D3DR 112 reconstructs a three-dimensional image from captured two-dimensional images, having the same activity-state (e.g., for each determined point of the heart timing cycle) and from the three-dimensional location and orientation data associated with each of the images.

AVDB 114 contains the reconstructed three-dimensional images of the inspected organ, along with the activity-state associated therewith and with the location and orientation of the coordinate system thereof. The detected ECG sequence is further used for synchronously playing back the three-dimensional images, where every three-dimensional image is displayed when the activity-state associated therewith is substantially equal to real-time detected activity-state of the inspected organ.

In case surgical tool 120 is inserted in the heart, superimposing processor 116 can add the three-dimensional location and orientation of surgical tool 120 to the reconstructed three-dimensional image. Alternatively, main computer 102 can extrapolate the shape of surgical tool 120 in the coordinate system of the reconstructed three-dimensional image.

Display 130 presents a three-dimensional motion picture of the inspected organ in synchrony therewith, which can be considered a pseudo real-time simulation thereof. It is noted that main computer 102 can determine the display reference coordinate system to be any of the following:

The coordinate system of the patient, where the body of the patient is still and the inspected organ and the surgical tool, move.

The coordinate system of the inspected organ, where the inspected organ is still, and surgical tool and the rest of body of the patient, move. It is noted that this viewing coordinate system can be extremely useful in cases where the inspected organ exhibits rapid movement.

The coordinate system of the surgical tool, where the surgical tool is still, and the inspected organ as well as the rest of the body of the patient, move.

Reference is now made to FIGS. 2A and 2B. FIG. 2A is an illustration in perspective of an inner-body radial ultrasound imaging system, generally referenced 170, constructed and operative in accordance with a further preferred embodiment of the present invention. FIG. 2B is an illustration in perspective of a plurality of radial two-dimensional images of the walls of an inspected vessel, generally referenced 190.

System 170 includes an Inner-body radial image transducer 172, a surgical tool (i.e., typically a minimal invasive surgical device) 174, MPS sensors 176 and 178, a mounting catheter 180 and a dilation catheter 182. It is noted that inner-body radial ultrasound imaging system 170 can be replaced with alternative ultrasound systems such as an inner-vascular ultrasound system (IVUS) which is discussed in further detail in FIG. 12 herein below, or other types of two-dimensional imaging systems.

Radial image transducer 172 is mounted on mounting catheter 180, which is further inserted in dilation catheter 182. MPS sensor 176 is located at a tip of mounting catheter 180 adjacent to radial image transducer 172. Mounting catheter 180 is inserted in dilation catheter 182. MPS sensor 178 is located in close proximity to the tip of surgical tool 174. Surgical tool 174 is further inserted in dilation catheter 182.

Radial image transducer 172 detects a plurality of two-dimension images of different areas of the inspected organ (such as two-dimensional images 190A, 190B, 190C, 190D, 190E and 190F (FIG. 2B). MPS system 108 (FIG. 1) detects the location and orientation of radial image transducer 172, using sensor 176. MPS system 108 (FIG. 1) further detects the location and orientation of surgical tool 174, using sensor 178. The location and orientation of two-dimensional images 190A, 190B, 190C, 190D, 190E and 190F (FIG. 2B) are directly derived from the location and orientation of the transducer 172.

As can be seen in FIG. 2B, each of the detected two-dimensional images 190A, 190B, 190C, 190D, 190E and 190F is two-dimensional representation of a different peripheral portion of the inspected area within the inspected organ and its vicinity. Radial image transducer 172 provides the detected two-dimension images 190A, 190B, 190C, 190D, 190E and 190F to two-dimensional image acquisition device 104 (FIG. 1). The System 100 associated between each two-dimensional image and the respective location and orientation.

Figure 3:
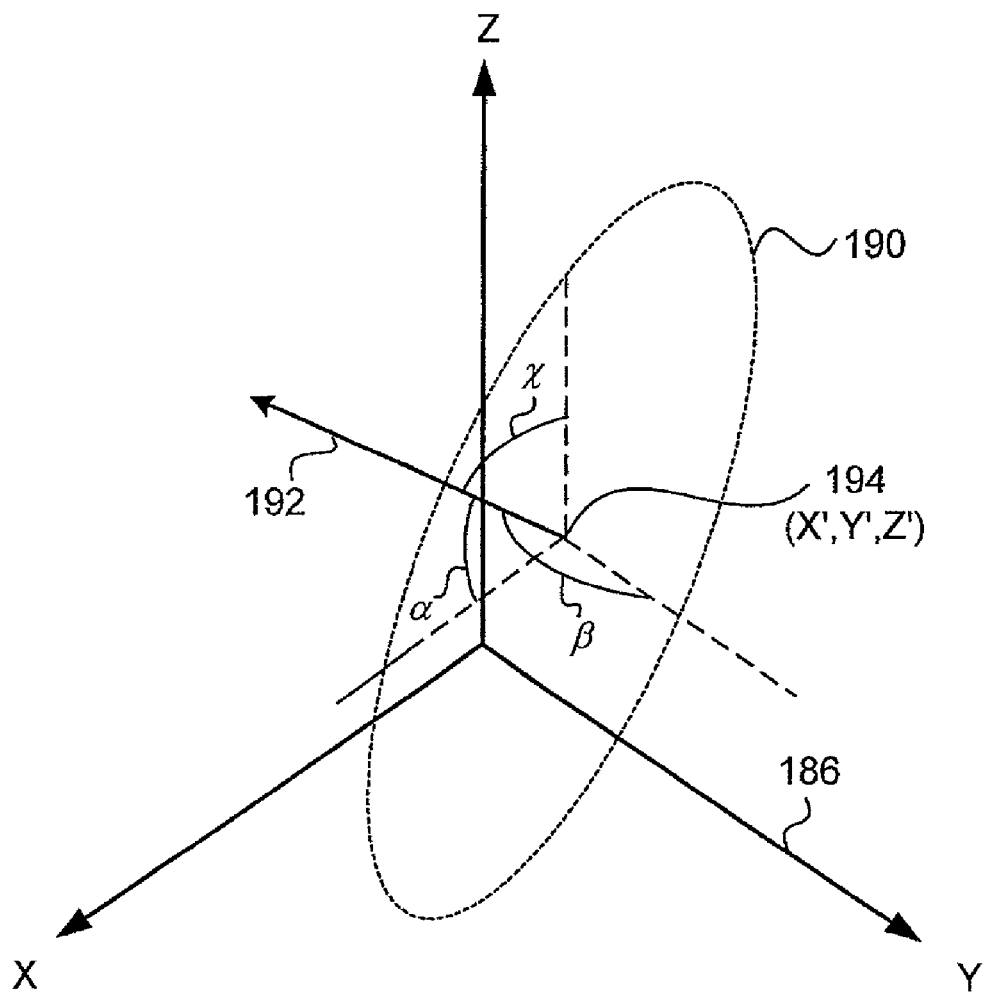
FIG. 3 is a schematic illustration of a two-dimensional image in a given coordinate system.

Reference is now made to FIG. 3, which is a schematic illustration of a two-dimensional image, generally referenced 190, in a given coordinate system, generally referenced 186. FIG. 3 is mainly used for visualizing the terms "location" and "orientation" of the two-dimensional image 190 in coordinate system 186.

The location and orientation of each two-dimensional image 190 are determined in the coordinate system 186 (X, Y and Z). System 100 determines a selected point in each captured two-dimensional image, which is to be the reference point for that image. In the example set forth in FIG. 3, the center of the image is determined to be the reference location point thereof. A unit vector extending from that point, perpendicular to the plane of that image determines the orientation of that image.

Each detected two-dimensional image 190 is taken in a specific location (X', Y' and Z') and a specific orientation (angles $\alpha$, $\beta$ and $\chi$) Vector 192 extends from a selected point 194 of the image 190. The coordinates of this point X', Y' and Z' determine the specific three-dimensional location of the image 190 in the coordinate system 186. Angles $\alpha$, $\beta$ and $\chi$ are the angles between the vector 192 and each of the axes X, Y and Z, accordingly. Thereby, vector 192 determines the specific three-dimensional orientation of the image 190 in the coordinate system 186.

Figure 4:
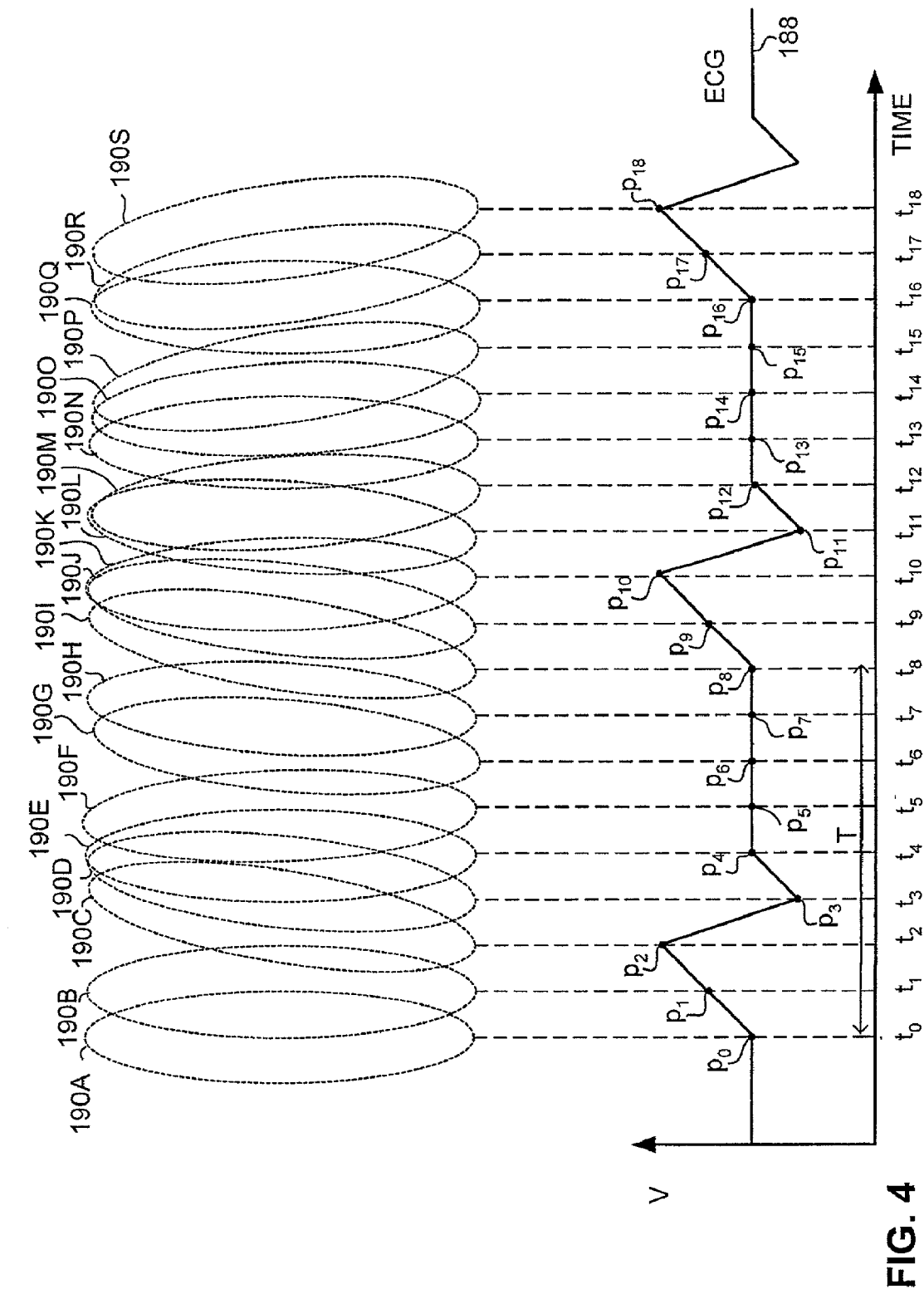
FIG. 4 is an illustration in perspective of a plurality of two-dimensional images and an organ timing signal.

Reference is now made to FIG. 4, which is an illustration in perspective of a plurality of two-dimensional images, generally referenced 190, and an organ timing signal, generally referenced 188. In the example set forth in FIG. 4, organ timing signal is an ECG signal.

The ECG signal can be used for synchronizing the detection procedure of two-dimensional images 190A, 190B, 190C, 190D, 190E, 190F, 190G, 190H, 190I, 190J, 190K, 190L, 190M, 190N, 190O, 190P, 190Q, 19OR and 190S, where each image is taken at a predetermined position in the organ timing signal. Two-dimensional images 190A, 190B, 190C, 190D, 190E, 190F, 190G, 190H, 190I, 190J, 190K, 190L, 190M, 190N, 190O, 190P, 190Q, 190R and 190S are detected at predefined points in time $t_0$, $t_1$, $t_2$, $t_3$, $t_4$, $t_5$, $t_6$, $t_7$, $t_8$, $t_9$, $t_{10}$, $t_{11}$, $t_{12}$, $t_{13}$, $t_{14}$, $t_{15}$, $t_{16}$, $t_{17}$ and $t_{18}$, respectively. T denotes the cycle duration of EGG signal 188 (e.g., the time interval between the time points $t_0$ and $t_8$) Each point $p_0$, $p_1$, $p_2$, $p_3$, $p_4$, $p_5$, $p_6$, $p_7$, $p_8$, $p_9$, $p_{10}$, $p_{11}$, $p_{12}$, $p_{13}$, $p_{14}$, $p_{15}$, $p_{16}$, $p_{17}$ and $p_{18}$ denotes a specific position on the ECG timing signal and is associated with specific activity-state of the heart.

In this example, two-dimensional images are detected continuously at a rate of eight images per ECG cycle into predetermined points in each heart cycle. Each point $p_0$, $p_1$, $p_2$, $p_3$, $p_4$, $p_5$, $p_6$ and $p_7$ denotes a specific position on the first ECG cycle, each point $p_8$, $p_9$, $p_{10}$, $p_{11}$, $p_{12}$, $p_{13}$, $p_{14}$ and $p_{15}$ denotes a specific position on the second ECG cycle, and the like. Points $p_8$ and $p_{16}$ have the same specific position on the ECG timing signal, as point $p_0$, and hence are associated with the same activity-state. Points $p_9$ and $p_{17}$ have the same specific position on the ECG timing signal, as point $p_1$, and hence are associated with the same activity-state. Points $p_{10}$ and $p_{18}$ have the same specific position on the ECG timing signal, as point $p_2$, and hence are associated with the same activity-state. Accordingly, each detected two-dimensional image is associated with a specific activity-state of the heart.

Figure 5B:
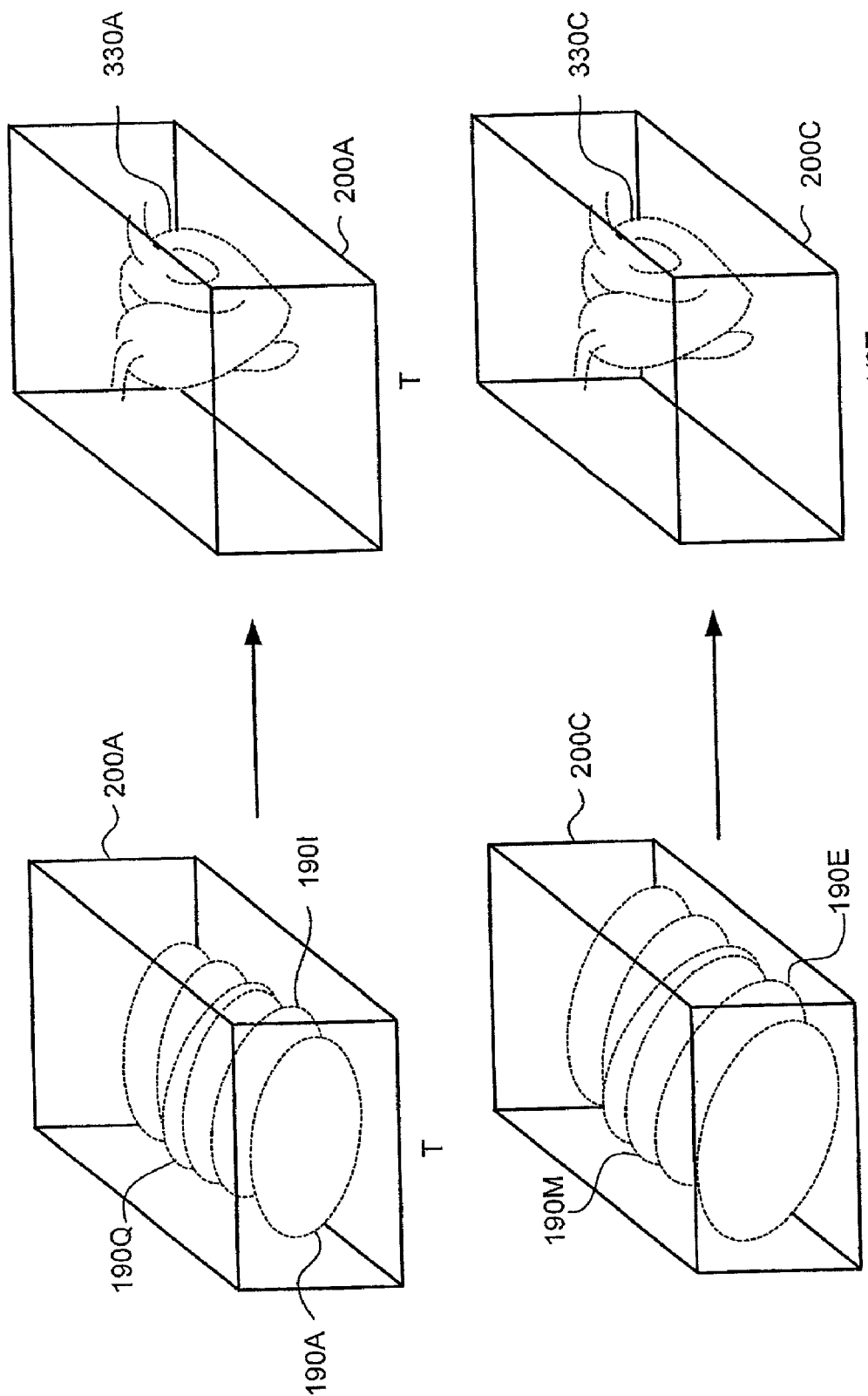
FIG. 5B is a schematic illustration of some of the three-dimensional volumes of FIG. 5A, at a later stage of image reconstruction.

Reference is now made to FIGS. 5A, 5B, 5C and 5D. FIG. 5A is a schematic illustration of a plurality of three-dimensional volumes, generally referenced 200, according to another preferred embodiment of the present invention. FIG. 5B is a schematic illustration of some of the three-dimensional volumes of FIG. 5A, at a later stage of image reconstruction. FIG. 5C is a schematic illustration of a selected three-dimensional volume of FIG. 5A, going through a procedure of image updating. FIG. 5D is a schematic illustration of a two-dimensional image, which includes foreign object information.

With reference to FIG. 5A, each of the three-dimensional volumes 200 is associated with a selected one of the specific positions in the organ timing signal cycle, and hence is associated with the respective activity-state. In the present example, three-dimensional volumes 200A, 200B, 200C and 200D are associated with organ timing signal cycle locations T, ¼T, ½T and ¾T, respectively.

Each of the three-dimensional volumes 200A, 200B, 200C and 200D is used for reconstructing a three-dimensional image for a selected location in the organ timing signal cycle, and hence for the respective activity-state. Main computer 102 (FIG. 1) sorts the two-dimensional images according to the timing position of the image on the ECG signal (i.e., specific activity-state).

In the present example, volume 200A includes two-dimensional images 190A, 190I and 190Q (FIG. 4), which were detected at time points $t_0$, $t_8$ and $t_{16}$, respectively. The position in the organ timing signal cycle of these images is T. Volume 200B includes two-dimensional images 190C, 190K and 190S (FIG. 4), which were detected at time points $t_2$, $t_{10}$ and $t_{18}$, respectively. The position in the organ timing signal cycle of these images is ¼ T. Volume 200C includes two-dimensional images 190E and 190M (FIG. 4), which were detected at time points $t_4$ and $t_{12}$, respectively. The position in the organ timing signal cycle of these images is ½ T. Volume 200D includes two-dimensional images 190G and 190O (FIG. 4), which were detected at time points $t_6$ and $t_{14}$, respectively. The position in the organ timing signal cycle of these images is ¾ T.

At this point, volume 200A contains information relating to the two-dimensional images that were stored therein, while portions of volume 200A remain at zero value, since no two-dimensional image is related thereto. D3DR 112 analyzes the content of three-dimensional volume 200A and attempts to determine the value of some of these zero value portions, for example, by means of extrapolation. With reference to FIG. 5B, D3DR 112 (FIG. 1) reconstructs image 330A within three-dimensional volume 200A. Similarly, D3DR 112 reconstructs image 330C within three-dimensional volume 200C.

System 100 (FIG. 1) updates the three-dimensional image 330A in real time. Main computer 102 (FIG. 1) continuously receives two-dimensional images, associated with a location and orientation thereof and an organ activity-state. Main computer 102 (FIG. 1) provides each of these two-dimensional images to D3DR 112 (FIG. 1) together with the three-dimensional volume, associated with the same organ activity-state. D3DR 112 updates the three-dimensional volume according to the values of the new two-dimensional images.

The update procedure can be performed in many ways. According to one aspect of the invention, a new value in a selected three-dimensional pixel (voxel) replaces an old value. According to another aspect of the invention, an updated voxel value includes a combination (linear or otherwise) of the old voxel value (i.e., which already exists in the three-dimensional volume) and the newly acquired value (i.e., received from the two-dimensional image). It is noted that system 100 can operate either using polygonal or voxel representations.

According to a further aspect of the invention, each of the voxels in the three-dimensional volume includes various attributes such as if the current value thereof, was provided from an acquired image, or was calculated in the process of reconstructing the three-dimensional image, by means of extrapolation. In this case, a newly acquired value is preferred over a calculated one.

With reference to FIG. 5C, D3DR 112 receives a new two-dimensional image 190Y, which is associated with an organ activity state of t=T. D3DR 112 updates the respective three-dimensional volume 200A and the image therein 330A, thereby producing an updated image $330A_{UPDATED}$.

In case where a surgical tool 120 (FIG. 1) is inserted in the inspected organ, the system 100 excludes a fragment of the two-dimensional image, which contains a representation of the surgical tool 120. Main computer 102 (FIG. 1) modifies the two-dimensional image by excluding these fragments (e.g. by introducing null values to those fragments). D3DR 112 analyzes the modified two-dimensional image and does not update the respective portions in the respective three-dimensional volume.

System 100 incorporates the ability to update the three-dimensional image sequence of the inspected object, in real time, even in the presence of foreign objects such as surgical tool 174 (FIG. 2A). According to a preferred embodiment of the invention, main computer 102 can determines according to the location and orientation of an acquired image and of surgical tool 174, if the surgical tool was included in the slice represented by the acquired image. With reference to FIG. 5D, two-dimensional image 190Z incorporates a small section 198, which is a representation of a portion of surgical tool 120, as determined from the location and orientation of MPS sensor 162₁. Two-dimensional image 190Z and section 198 define a section 199, in which section 198 is excluded from two-dimensional image 190Z. According to real-time updating procedure of the three-dimensional image sequence which was described in connection with FIG. 5D, system 100 updates only section 199 to the respective three-dimensional image. Hence, when the surgical tool is removed from the body of the patient, it leaves no traces in the reconstructed three-dimensional images.

It is noted that each ECG cycle consists of a period of relaxation, named a diastole followed by a period of contraction named a systole. Duration of the ECG cycle is defined as a time between two subsequent heart contractions. According to a further preferred embodiment, the ECG cycle is evenly divided by N, where N denotes the number of three-dimensional images in the final image sequence.

Figure 6:
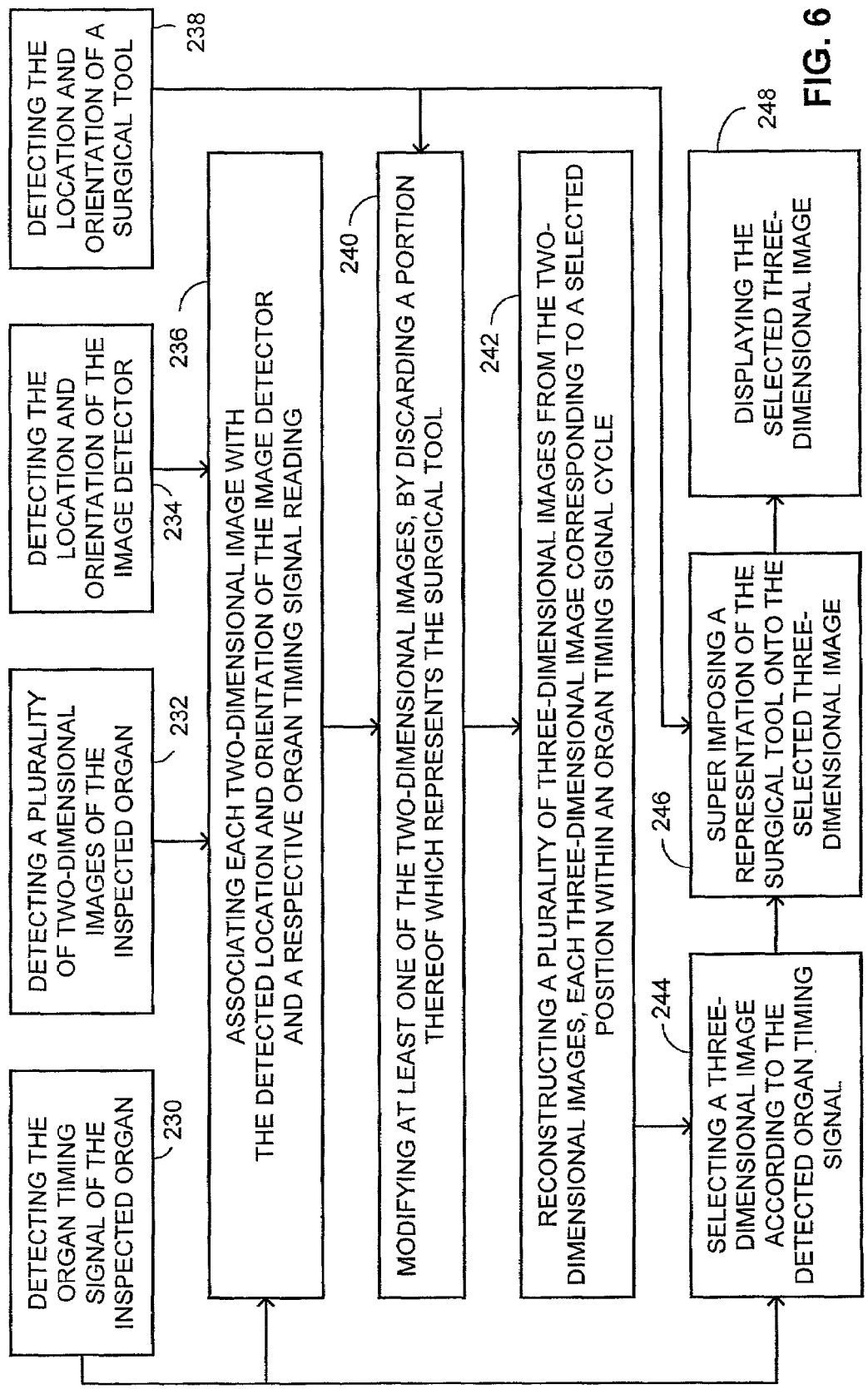
FIG. 6 is a schematic illustration of a method for operating the three-dimensional imaging system of FIG. 1, operative in accordance with a further preferred embodiment of the presented invention.

Reference is now made to FIG. 6, which is a schematic illustration of a method for operating the three-dimensional imaging system 100, operative in accordance with a further preferred embodiment of the presented invention.

In step 230, the timing signal of an inspected organ is detected. The detection is performed by a medical monitoring device, which is selected according to the inspected organ. For example, if the inspected organs are blood vessels, then the medical device can be any conventional stent delivering system, a balloon mechanism, and the like.

If the inspected organ is the heart, then the medical device is an ECG monitor. If the inspected organs are the lungs, then the medical device is a respiratory rate monitor. Special devices can be constructed for detecting the movement of the eye lid, the eye, and the like. For example, an MPS sensor can be attached to the eye lid for detecting the movement thereof. With reference to FIG. 1, ECG monitor 106 detects the organ timing signal through ECG-electrodes 128.

In step 232, a plurality of two-dimensional images of the inspected organ is detected. With reference to FIG. 1, two-dimensional image acquisition device 104 detects a plurality of two-dimensional images of the inspected organ through image transducer 118.

In step 234, the three-dimensional location and orientation of the image detector is detected. With reference to FIG. 1, MPS system 108 detects the three-dimensional location and orientation of the image detector using MPS sensor 162₂, mounted thereon.

In step 236, each detected two-dimensional image is associated with the location and orientation information thereof and the organ timing signal at the time the two-dimensional image was taken. With reference to FIG. 1, main computer 102 receives the ECG signal, the acquired two-dimensional images and the location and orientation of each two-dimensional image. Main computer 102 associates each detected image with the location and orientation information thereof and the organ-timing signal.

In step 238, the location and orientation of a surgical tool are detected. With reference to FIG. 1, MPS system 108 detects the location and orientation of surgical tool 120, via MPS sensor 162₁.

In step 240, the two-dimensional images are modified by discarding a portion thereof, which represents the surgical tool. It is noted that two-dimensional images which are located in planes which do not intersect the surgical tool, do not include any image respective thereof and hence remain unchanged. With reference to FIGS. 1 and 5D, main computer 102 estimates the portion within an acquired two-dimensional image, such as two-dimensional image 190Z, that might include a representation of the image of surgical tool 120. Main computer 102 performs that estimation according to the detected location and orientation of surgical tool 120. Main computer 102 determines a three-dimensional space which is occupied by surgical tool 120, according to the information which MPS sensor 162₁ acquires and according to data respective of the physical dimensions of surgical tool 120. Main computer 102 calculates an intersection area (e.g., portion 198 as illustrated in FIG. 5D), in which an acquired two-dimensional image (e.g., reference 190Z in FIG. 5D) and that three-dimensional space intersect. Main computer 102 discards that intersection area for example, by changing the values thereof to null values. Discarding of the image of surgical tool 120 from the two-dimensional images, is necessary in order to reconstruct a three-dimensional image of the inspected organ, free of artifacts such as the image of surgical tool 120.

In step 242, a three-dimensional image is reconstructed. The reconstruction includes three procedures. The first procedure is sorting the two-dimensional images into groups, according to their respective timing position (i.e., activity-state) within the organ timing signal. With reference to FIG. 1 main computer 102 sorts the two-dimensional images according to the image timing position in the organ timing signal cycle.

The second procedure is the placing of all of the two-dimensional images of a selected group in a three-dimensional virtual volume (such as a three-dimensional matrix), according to their respective location and orientation. With reference to FIG. 1, main computer 102 stores each two-dimensional image in a selected one of the three-dimensional virtual volumes 200 (FIG. 5A) within adaptive volumetric database 114.

The third procedure is filling the missing parts in the three-dimensional virtual volumes, for example, by means of interpolation. With reference to FIG. 1, D3DR 112 reconstructs a three-dimensional image in each of the three-dimensional virtual volumes 200 (FIG. 5B), from the two-dimensional images stored therein.

In step 244, a three-dimensional image is selected according to the organ timing signal detected in step 230. With reference to FIGS. 1 and 4, ECG monitor 106 detects the organ timing signal 188 of the inspected organ via ECG-electrodes 128. Main computer 102 selects three-dimensional images according to a real time detected organ timing signal. The selected three-dimensional image has to be associated with the position in the organ timing signal cycle, as the position of the real time detected organ timing signal cycle.

In step 246, a representation of the surgical tool is added to the selected three-dimensional image. With reference to FIG. 1, MPS sensor 162₁ detects the location and orientation of surgical tool 120 Superimposing processor 116 adds a representation (e.g., a symbol) of surgical tool 120, to the selected three-dimensional image. Superimposing processor 116 adds the representation according to the location and orientation of surgical tool 120, which MPS sensor 162₁ detects in step 238. Since the location and orientation of the surgical tool and the location and orientation of the acquired images, are all detected using the same MPS system, all reside in a single coordinate system and hence do not have to be correlated.

Figure 8:
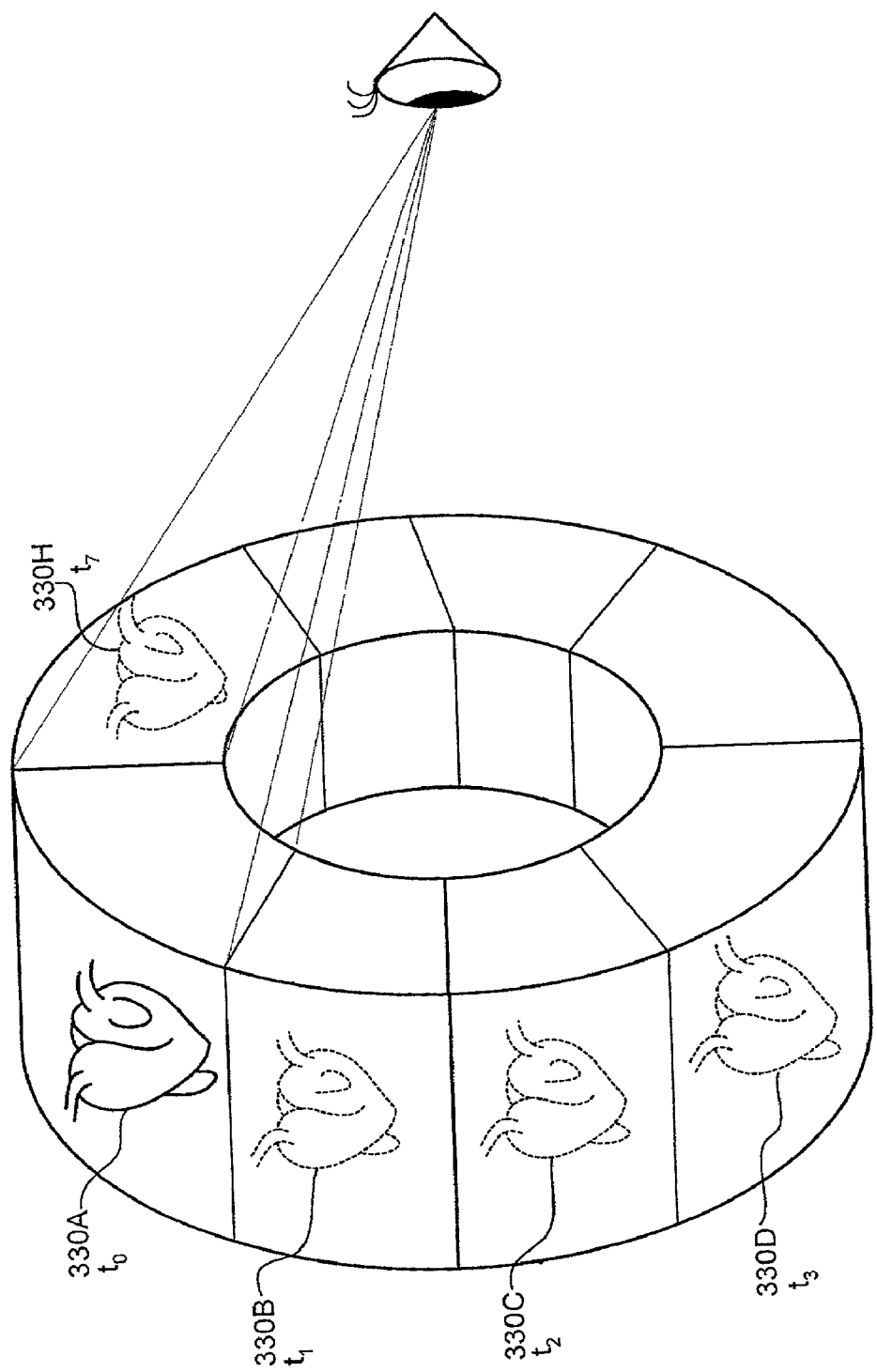
FIG. 8 is an illustration in perspective of a cyclical sequence of three-dimensional images, according to a further preferred embodiment of the present invention.

In step 248, the selected three-dimensional image is displayed. With reference to FIGS. 1 and 8, display 130 displays the selected three-dimensional images in a sequence, according to the real time detected organ timing signal cycle. For example, the operator can view a video of the heart of the patient, which corresponds to the real time detected heartbeat of the patient and at the same time, hear this heartbeat through a stethoscope.

Figure 7A:
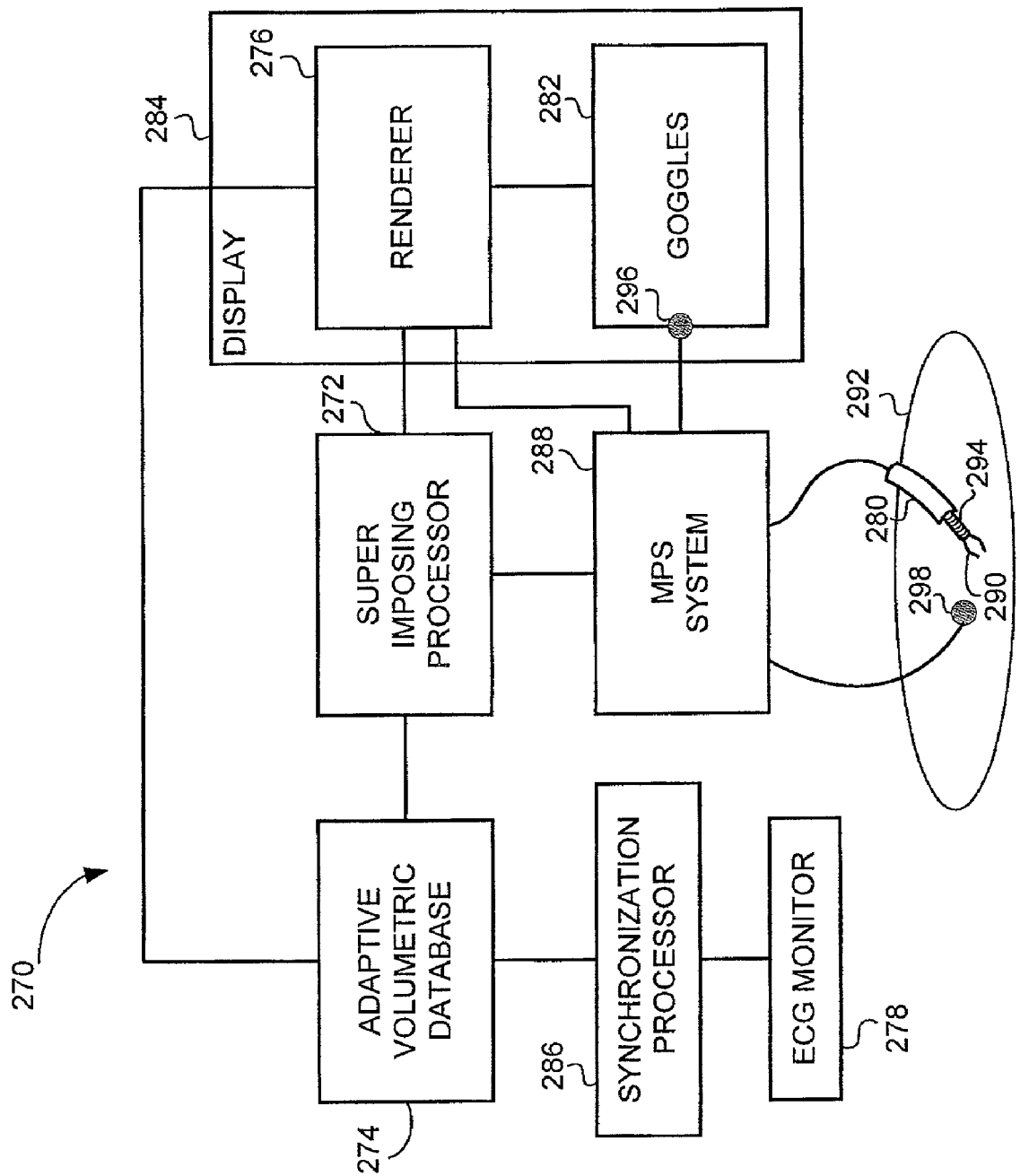
FIG. 7A is a schematic illustration of a real-time three-dimensional display playback system, constructed and operative in accordance with another preferred embodiment of the present invention.
Figure 7B:
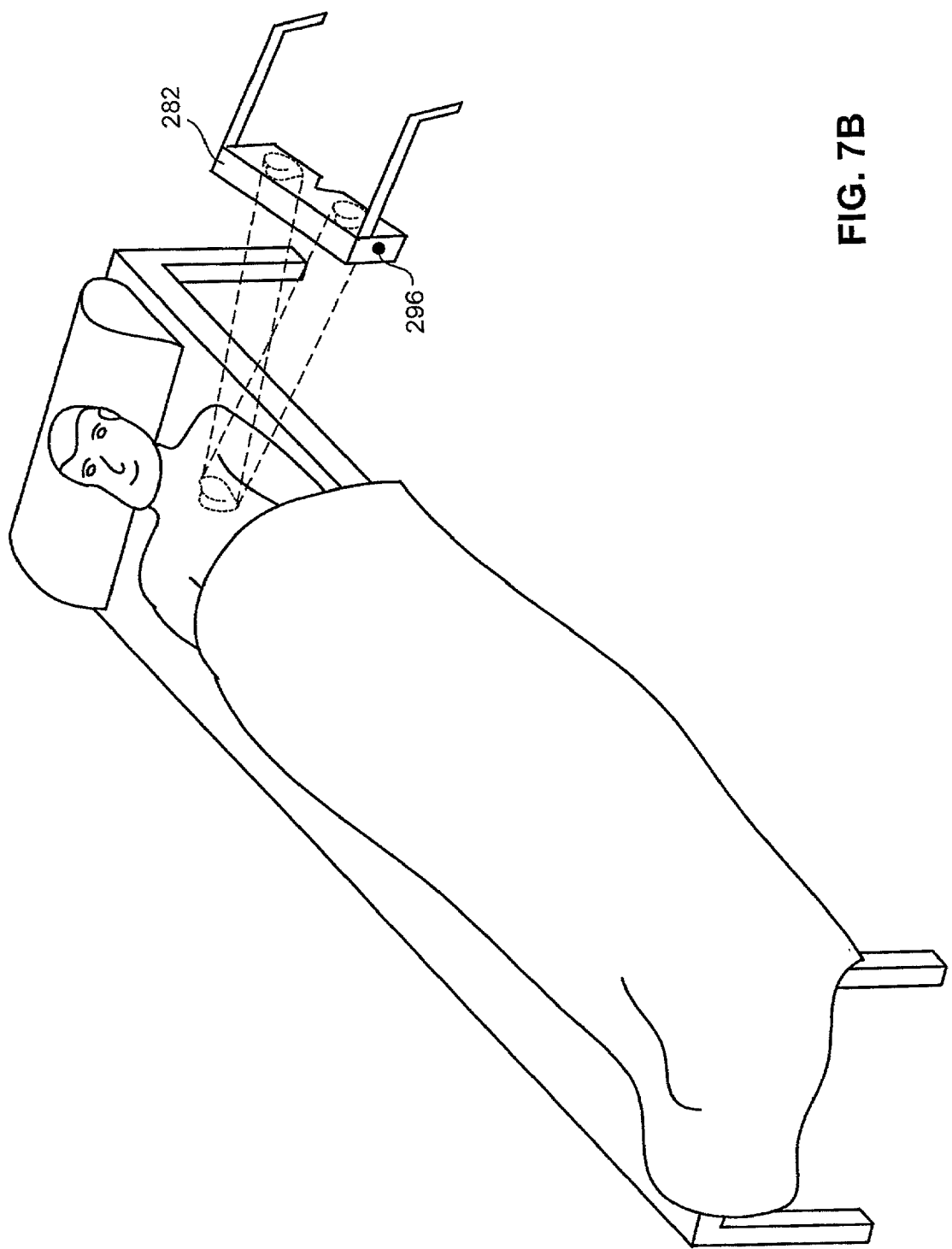
FIG. 7B is a schematic illustration of the goggles of FIG. 7A, displaying a three-dimensional image of the heart of a patient.

Reference is now made to FIGS. 7A and 7B. FIG. 7A is a schematic illustration of a real-time three-dimensional display playback system, generally referenced 270, constructed and operative in accordance with another preferred embodiment of the present invention. FIG. 7B is a schematic illustration of the goggles of FIG. 7A, displaying a three-dimensional image of the heart of a patient.

With reference to FIG. 7A, system 270 includes a superimposing processor 272, an adaptive volumetric database (AVDB) 274, an ECG monitor 278, a display 284, a synchronization processor 286, a medical positioning system (MPS) 288, a dilation catheter 280 and a plurality of MPS sensors 294, 296 and 298. Display 284 includes a renderer 276 and goggles 282. A surgical tool 290 is inserted into dilation catheter 280.

Superimposing processor 272 is connected to AVDB 274, renderer 276 and to MPS system 288. Renderer 276 is further connected AVDB 274 and to goggles 282. MPS system 288 is further connected to dilation catheter 280, renderer 276 and to MPS sensors 294, 296 and 298. Synchronization processor 286 is connected to AVDB 274 and to ECG monitor 278.

ECG monitor 278 detects the organ timing signal of the inspected organ and provides this signal to synchronization processor 286. The detected organ timing signal is used for synchronizing between a sequence of three-dimensional images and the movement of the inspected heart.

Synchronization processor 286 analyzes the ECG signal, and determines activity-states therein. Synchronization processor 286 provides a retrieval command to AVDB 274, to retrieve an image record, according to the currently detected activity-state.

AVDB 274 contains a sequence of three-dimensional images of the inspected organ, along with an activity-state associated therewith and with the location and orientation of the coordinate system thereof. It is noted that this sequence of three-dimensional images can be acquired using system 100 (FIG. 1) or any other system for acquiring three-dimensional images (e.g., MRI, X-rays, and the like).

AVDB 274 selects a three-dimensional image of the organ, which is associated with the specific activity-state according to the received retrieval command. This three-dimensional image can be rendered and displayed as is, in synchrony with the organ timing signal. In the example, where the inspected organ is the heart, the physician is presented with an image sequence, which is real-time synchronized with the ECG signal The physician, as he uses his stethoscope to hear the heart beats, can see a moving visual representation of the heart, at the same time.

Renderer 276 can render the three-dimensional image according to reference coordinates of surgical tool 290, reference coordinates of the inspected organ, or reference coordinates of the body of the patient. The selected reference coordinates define a stationary reference coordinate system, in which all other objects may move.

For example, if the coordinates of surgical tool 290 are selected as reference, then renderer 276 renders the three-dimensional image so that the surgical tool is stationary and the heart moves relative thereto. Accordingly, when the physician moves surgical tool 290 relative to the inspected organ, she observes a stationary representation of surgical tool 290, while the inspected organ exhibits movement due to the motion of the inspected organ relative to the representation of surgical tool 290.

On the contrary, if the coordinates of the inspected organ are selected as reference, then renderer 276 renders the three-dimensional image so that the inspected organ is stationary and surgical tool 290 moves relative thereto. Accordingly, when the physician moves surgical tool 290 relative to the inspected organ, she observes a stationary image of the inspected organ, while surgical tool 290 exhibits movement due to the motion of the representation or surgical tool 290 relative to the inspected organ.

MPS system 288 includes an MPS transmitter (not shown) and MPS sensors 294, 296 and 298. MPS system 288 determines the location and orientation of surgical tool 290, using sensor 294 mounted thereon. MPS system 288 determines the location and orientation of the point of view of the user, using MPS sensor 296 (FIG. 7B), mounted on goggles 282. MPS system 288 determines the location and orientation of the body of the patient using MPS sensor 298, attached thereto.

Superimposing processor 272 receives the selected three-dimensional image of the heart from AVDB 274. Superimposing processor 272 further receives parameters related to the location and orientation of surgical tool 290 and parameters related to the location and orientation of reference points on the body of the patient, from MPS system 288.

Superimposing processor 272 uses the location and orientation of the reference points to align the coordinate system of the three-dimensional images with the coordinate system of surgical tool 290. Superimposing processor 272 adds a representation of surgical tool 290 to the three-dimensional image of the heart and provides this image to renderer 276.

Renderer 276 receives parameters related to the location and orientation of goggles 282 and the parameters related to the location and orientation of the reference points of the body of the patient, from MPS system 288. Renderer 276 uses these parameters to determine a viewing plane, and renders the three-dimensional images to that viewing plane. Renderer 276 provides the rendered images to goggles 282.

Goggles 282 (FIG. 7B) are preferably see-through, so that they are semi-transparent, in a way that the physician can actually see the body of the patient as well as an image projected on the goggle screens. System 270 (FIG. 7A) determines a projection plane on the body of the patient, according to the location and orientation of the body of the patient and of goggles 282. System 270 displays the three-dimensional image sequence using goggles 282 so that it is perceived to be within the body of the patient, as actually seen by the physician through the goggles 282.

Reference is now made to FIG. 8, which is an illustration in perspective of a cyclical sequence of three-dimensional images, according to a further preferred embodiment of the present invention. The sequence is presented, image by image to a user, so as to produce an illusion of a moving image. The intermediate presented three-dimensional image is selected according to a real-time detected specific location in the organ timing signal cycle.

With reference to FIG. 7, AVDB 274 selects three-dimensional images continuously, at a rate of eight images per each heart cycle. Synchronization processor 286 provides a retrieval command to AVDB 274, according to the currently detected specific position in the organ timing signal cycle. AVDB 274 retrieves three-dimensional images 330A, 330B, 330C, 330D and 330H according to selected points $t_1=0$, $t_1=\frac{1}{8}T$, $t_2=\frac{2}{8}T$, $t_3=\frac{3}{8}T$, $t_4=\frac{4}{8}T$ and $t_7=\frac{7}{8}T$ within the heart timing signal (FIG. 4), respectively. As stated above, each three-dimensional image 330 is associated with the specific activity-state of the heart. Hence, playing images 330A, 330B, 330C, 330D and 330H in cyclic sequence provides a pseudo realistic illustration of the motion of the organ (i.e., due to the repetitive nature of the periodic cardiac motion).

Figure 9:
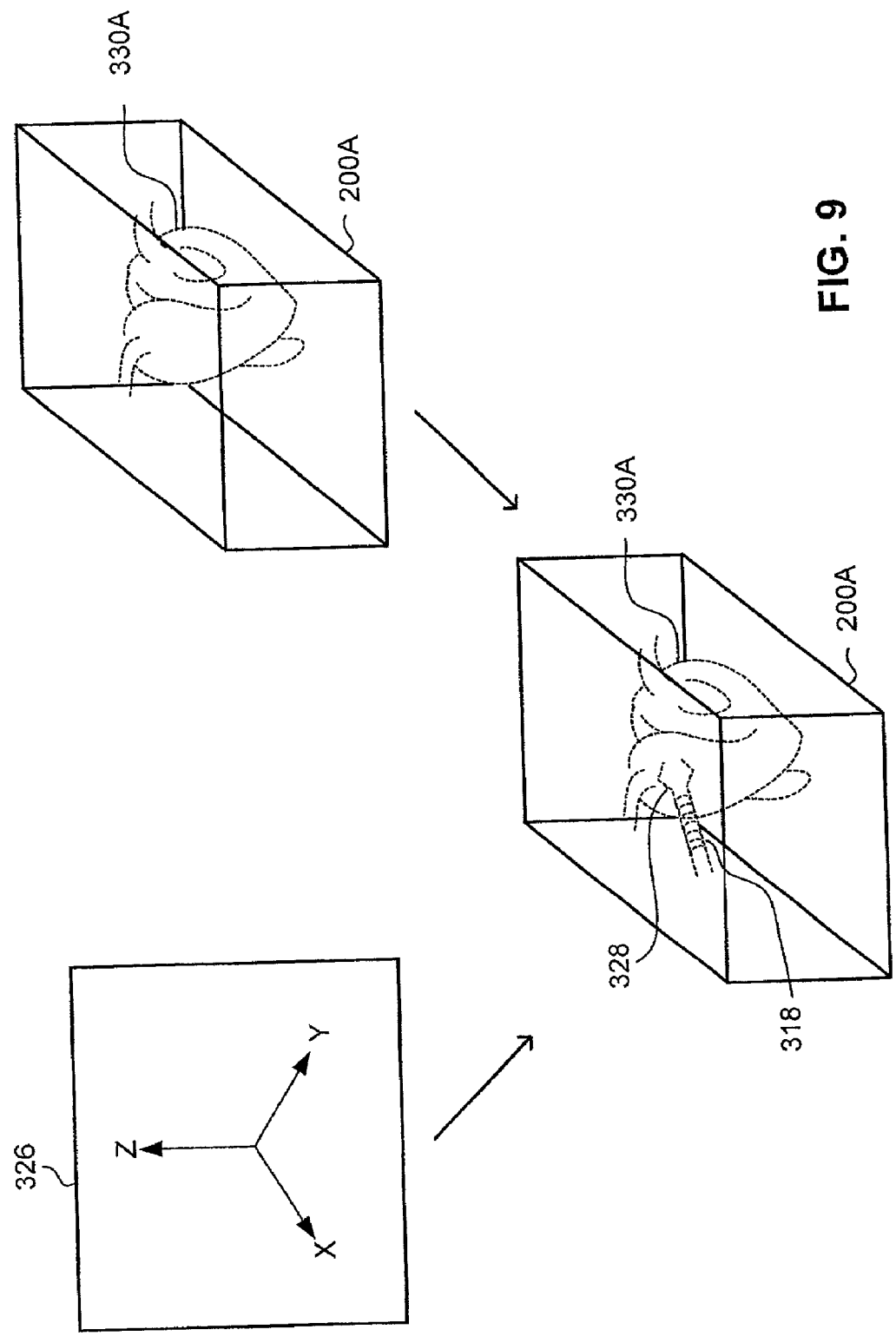
FIG. 9 is a schematic illustration of a superimposing process, operative in accordance with another preferred embodiment of the present invention.

Reference is now made to FIG. 9, which is a schematic illustration of a superimposing process, operative in accordance with another preferred embodiment of the present invention. The system 270 (FIG. 7) introduces a representation of the currently used surgical tool 328 to each selected image, such as image 330A. This representation can either be a minimal one (e.g., in the form of a cursor) or an elaborated one which provides pseudo realistic visualization of that surgical tool.

The location and orientation of three-dimensional image 330A are determined in a coordinate system 326 (X, Y and Z). Similarly, the location and orientation of a MPS sensor 318, and hence the location and orientation of a surgical tool 328 are also determined in the coordinate system 326 (X, Y and Z). Accordingly, a real-time representation of surgical tool 328 can be added to tree-dimensional image 330A. With reference to FIG. 7, superimposing processor 272 adds the representation of surgical tool 328 to selected three-dimensional image 330A, which was reconstructed in thee-dimensional volume 200A. It is noted that the surgical tool can be any conventional tool (e.g., clamp, laser cutter, brush, catheter, stent, balloon, pace maker electrode, solution dispensing unit, neuron electrode, substance collection unit, surgical delivery tool (e.g., for delivering genes, drugs, devices and the like), and the like). for example, a device delivery tool can be a medical tool for delivery of a medical device, such as a permanent stent, a removable stent, and the like, to the body of the patient.

The present invention allows the physician to operate on a dynamically moving object such as the heart, with a real-time representation surgical tool that he is using.

Figure 10:
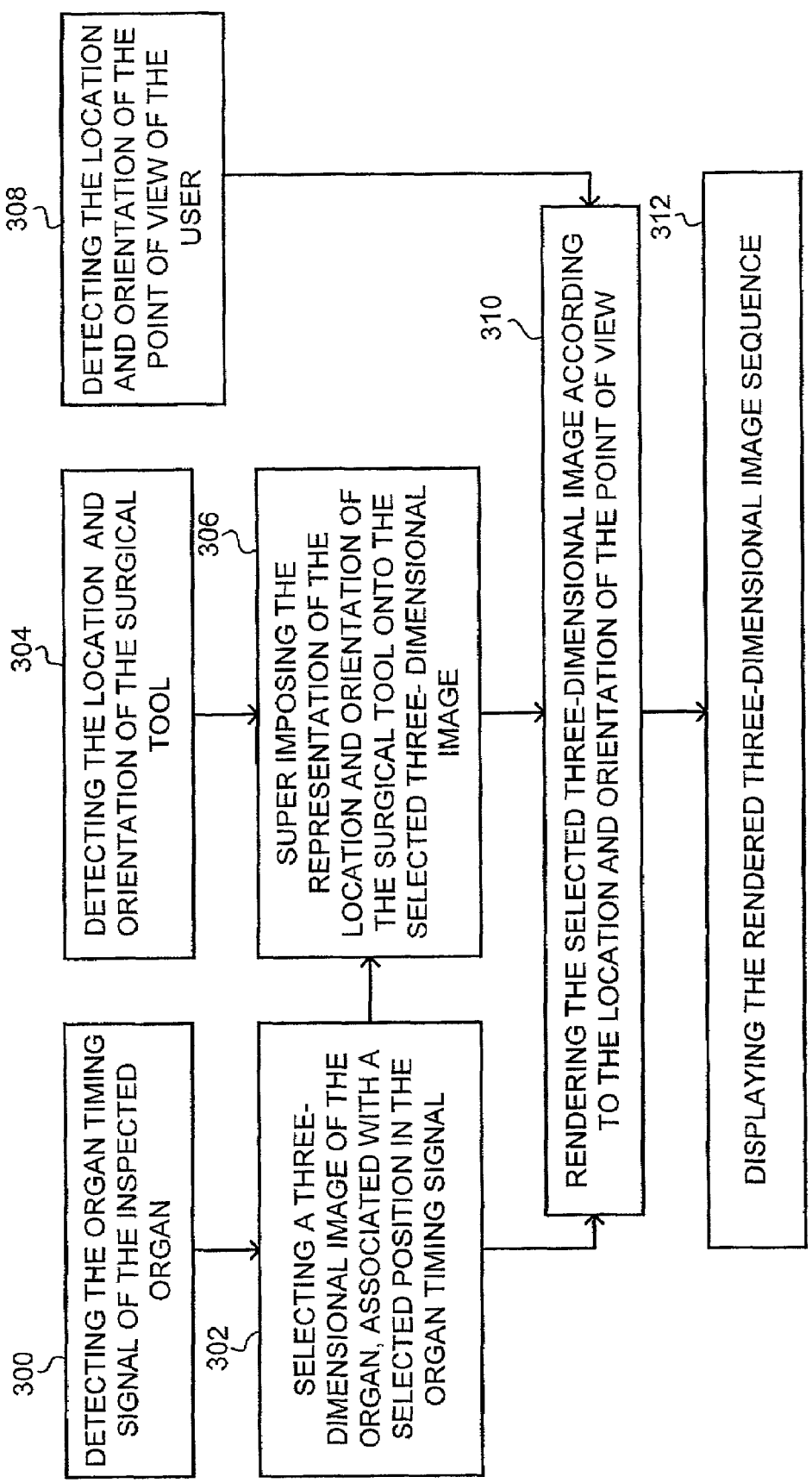
FIG. 10 is a schematic illustration of a method for operating the system of FIG. 7A, operative in accordance with a further preferred embodiment of the present invention.

Reference is now made to FIG. 10, which is a schematic illustration of a method for operating system 270, operative in accordance with a further preferred embodiment of the present invention. In step 300, an organ timing signal of the inspected organ is detected. According to the present invention, the system 100 (FIG. 1) includes a medical monitoring device, which is selected according to the inspected organ. Such device detects a time dependent signal of the organ, which is associated with an organ movement. With reference to FIG. 7, ECG monitor 278 detects the heart-timing signal.

In step 302, a three-dimensional image of the organ (e.g., the heart), associated with a selected timing point within the organ timing signal is selected. With reference to FIG. 7, AVDB 274 selects the three-dimensional image of the organ.

In step 304, the location and orientation of a surgical tool, are detected. Detection of the location and orientation of a surgical tool can be performed by methods known in the art, such as magnetic fields, ultrasound triangulation or radiation, inertial sensor—dead reckoning sensor, and the like. With reference to FIG. 7, MPS system 288 detects the location and orientation of surgical tool 290, using sensor 294 mounted thereon.

In step 306, a representation of the location and orientation of the surgical tool is superimposed onto the selected three-dimensional image. With reference to FIG. 7, superimposing processor 272 superimposes parameters related to location and orientation of the surgical tool onto the selected three-dimensional image.

In step 308, the location and orientation of the point of view of the user, are detected. The location and orientation of the point of view of the user are derived from the location and orientation of goggles 282. Parameters of the location and orientation of goggles 282 determine a viewing plane of the user. System 270 can determine two adjacent viewing planes, one for each LCD element of the goggles (one for each eye). With reference to FIG. 7, MPS system 288 detects the location and orientation of goggles 282, using sensor 296 mounted thereon. It is noted that more than one display unit (i.e., goggles) can be introduced to the system, employing a different MPS sensor, mounted thereon.

In step 310, the selected three-dimensional image is rendered according to the location and orientation of the point of view of the user. With reference to FIG. 7, renderer 276 renders the selected three-dimensional image according to the location and orientation of the point of view.

In step 312, a rendered three-dimensional image sequence (i.e., a three-dimensional motion picture) is displayed. The three-dimensional motion picture of the inspected organ can be displayed on any type of display, monoscopic, stereoscopic or holographic (e.g., a video monitor, goggles, holographic generator, and the like). With reference to FIG. 7, goggles 282 displays a rendered three-dimensional image sequence.

Figure 11:
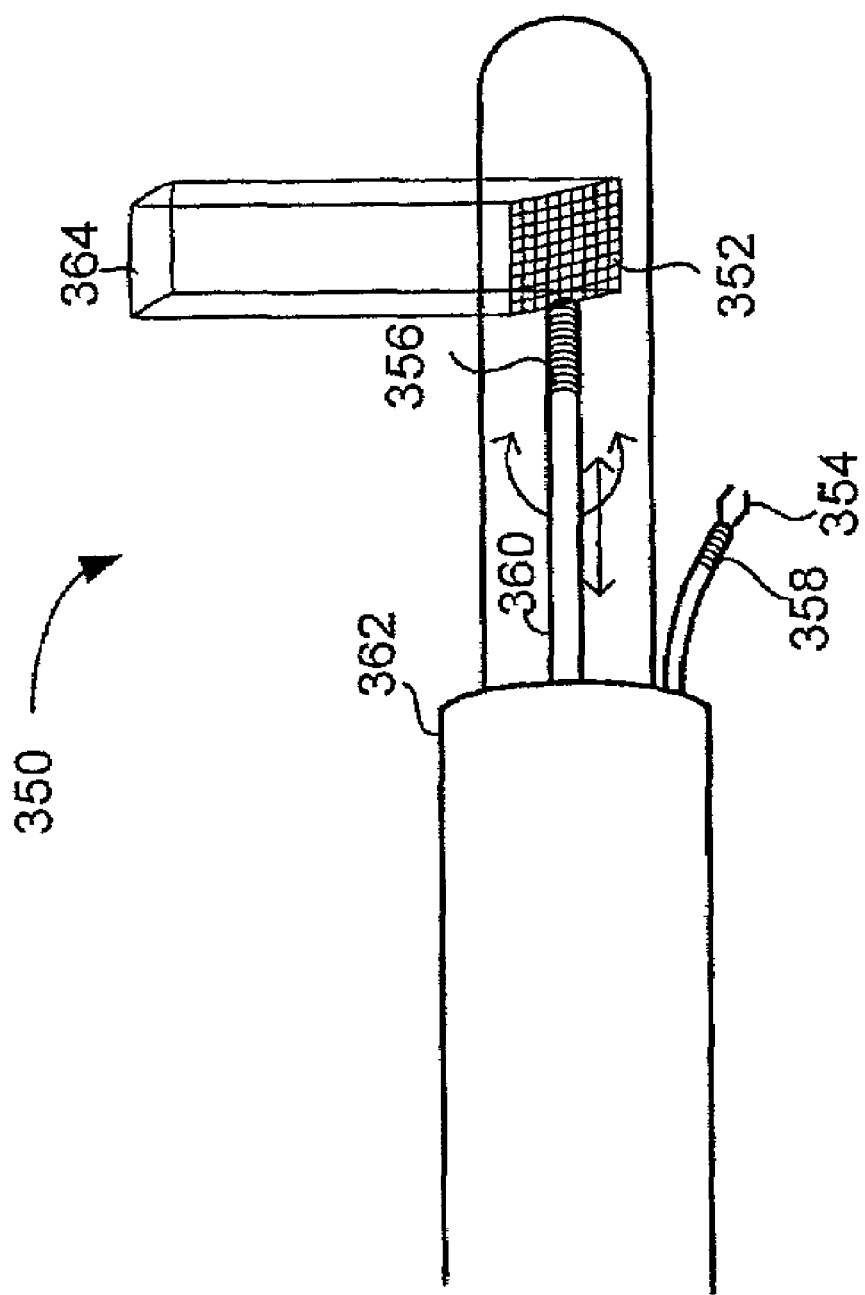
FIG. 11 is an illustration in perspective of an innervascular imaging and surgery system, constructed and operative in accordance with another preferred embodiment of the invention.

Reference is now made to FIG. 11, which is an illustration in perspective of an inner-vascular imaging and surgery system, generally referenced 350, constructed and operative in accordance with another preferred embodiment of the invention.

Inner-vascular imaging and surgery system 350 includes an inner-vascular ultrasound system (IVUS) transducer 352, a surgical tool (i.e., typically a minimal invasive surgical device) 354, MPS sensors 356 and 358, a mounting catheter 360 and a dilation catheter 362. IVUS transducer 352 is mounted on mounting catheter 360. It is noted that other IVUS devices, such as ones which include rotary acoustic mirrors, are also applicable to this embodiment.

IVUS transducer 352 produces ultrasound waves and directs them at the wall of a tubular organ (not shown), covering a surface referenced 364. Surface 364 reflects a portion of the ultrasonic waves directed thereto. IVUS transducer 352 detects these reflected ultrasonic waves and provides a respective signal to an image processing system (not shown) connected thereto. A conventional image processing system reconstructs a single three-dimensional image from all of the two-dimensional image, according to the location and orientation of each of them. According to the present invention, image processing system reconstructs a plurality of three-dimensional images, each for a different position in the timing cycle of the organ timing signal.

It is noted, that the IVUS is used for imaging the interior of coronary arteries during diagnosis, clinical treatment and performing research. This system provides a comprehensive and detailed understanding of the coronary arteries (or other blood vessels). A conventional IVUS detector is, for example, the Ultra-Cross system, manufactured by Boston Scientific Scimed or the In-Vision system, manufactured by Jomed USA (aka Endosonics) both companies located in San-Diego, Calif. USA. These systems are mainly used for slicing images of coronary images.

The present invention provides a novel structure, for producing a qualitative model of the blood vessel, using a combination of conventional IVUS elements and the unique miniature MPS sensor. According to a further preferred embodiment of the invention, the IVUS image sequence can be visually stabilized using the ECG signal. A selected time point in the ECG signal cycle, determines the momentary local blood pressure in the blood vessel, which in turn determines the momentary diameter of that blood vessel for that position within the cycle. Hence, the visual diameter of the blood vessel can be adjusted artificially, by means of image processing, so as to present a steady image of the blood vessel during the surgical procedure.

In general, the IVUS system produces a "road map" in which the surgeon navigates. Other imaging methods can also be used for producing such a road map, which can be stored in the volumetric database and played back according to the method of the invention, such as 3D ANGIUM, and the like.

Figure 12:
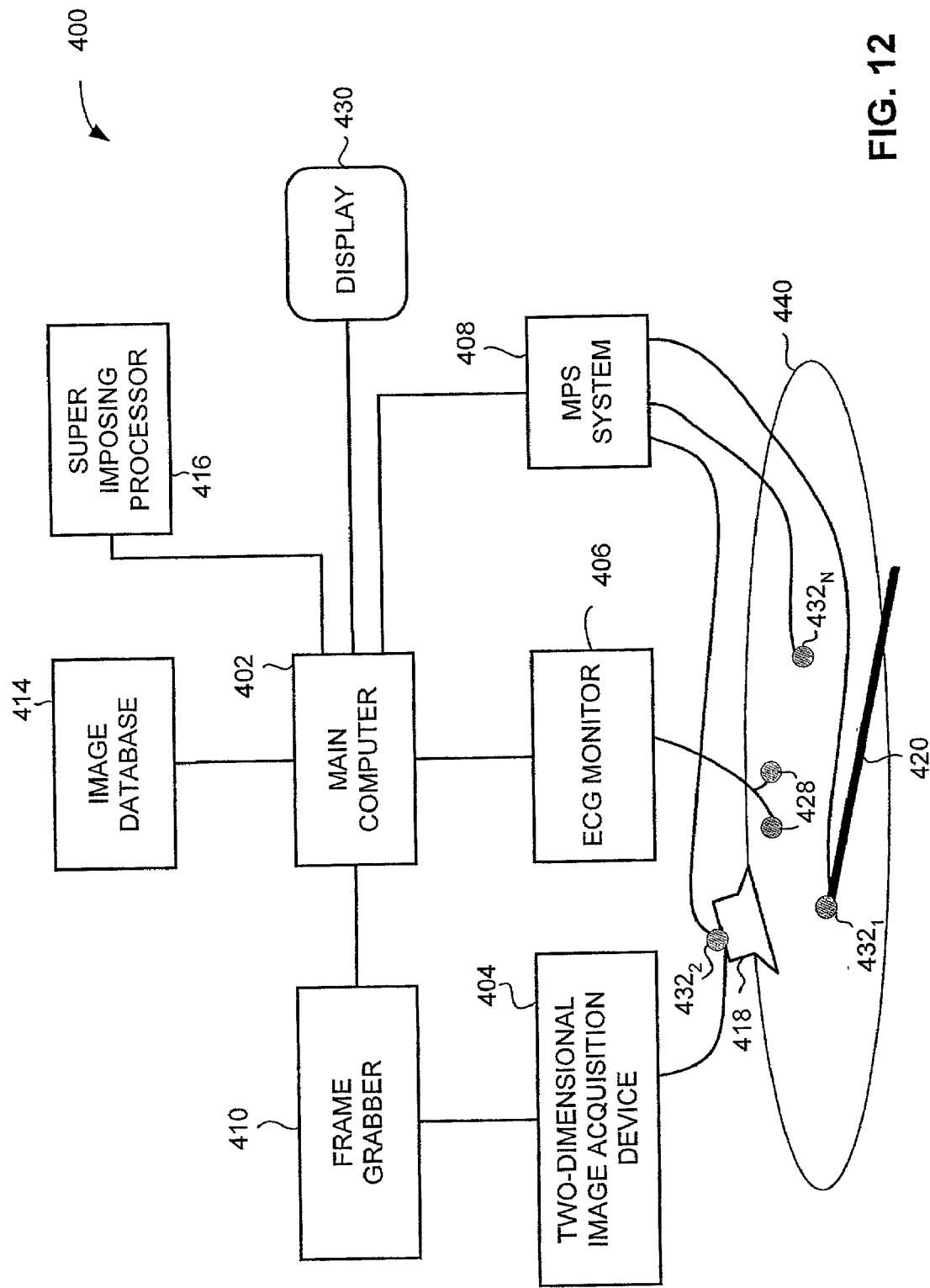
FIG. 12 is a schematic illustration of a multi function two-dimensional imaging system, constructed and operative in accordance with a further preferred embodiment of the present invention.

Reference is now made to FIG. 12, which is a schematic illustration of a multi function two-dimensional imaging system, generally referenced 400, constructed and operative in accordance with a further preferred embodiment of the present invention. In the example set forth in FIG. 12, system 400 is adapted for producing a two-dimensional image sequence of the heart and playing it in real time in synchrony with the motion of the heart.

Two-dimensional imaging system 400 includes, a main computer 402, a two-dimensional image acquisition device 404, an ECG monitor 406, a medical positioning system (MPS) 408, a frame grabber 410, an image database 414, a superimposing processor 416, a surgical tool 420, a plurality of MPS sensors $432_1$, $432_2$ and $432_N$, and a display 430.

Two-dimensional image acquisition device 404 includes an image transducer 418. ECG monitor 406 continuously detects an electrical timing signal of the heart during inspection or surgery, by employing a plurality of ECG electrodes 428.

Main computer 402 is connected to ECG monitor 406, MPS system 408, frame grabber 410, superimposing processor 416 and to display 430. Two-dimensional image acquisition device 404 is connected to frame grabber 410. MPS system 408 includes an MPS transmitter (not shown) and sensors MPS $432_1$, $432_2$ and $432_N$.

System 400 is directed at capturing and playing a two-dimensional image sequence of the inspected organ, with a superimposed representation of the projection of the surgical tool 420. Transducer 418 detects a plurality of two-dimensional images of the inspected organ and provides them to two-dimensional image acquisition device 404, which further transfers them to frame grabber 410. Frame grabber 410 grabs each detected two-dimensional image and provides it to main computer 402, which stores them in image database 414, along with an organ timing signal, as received from the ECG monitor 406. The images can be used at any time to produce a two-dimensional cyclic image sequence of a selected plane of the inspected organ. System 400 can synchronize this image sequence with a real-time reading of the timing signal of the inspected organ, using procedures similar to those described above.

The example set forth in FIG. 12 includes MPS sensor $432_2$, which detects the location and orientation of transducer 418 for each of the acquired images and MPS system 408, which determines if all of the acquired images reside on the same plane. If not, then MPS system 408 can indicate to the user a detected deviation from a given plane, either visually, audibly or mechanically (e.g., by means of vibration, and the like). It is noted that a simpler version of system 400, according to a further preferred embodiment, does not include an MPS sensor attached to the transducer.

MPS sensor $432_1$ detects the location and orientation of surgical tool 420. MPS system 408 determines the location and orientation of surgical tool 420 and provides this information to main computer 402, which in turn provides it to super-imposing processor 416. Superimposing processor 416 determines a representation in space, of the surgical tool 420, derives a projection thereof, onto the plane of the detected images and superimposes that projection with each of the images in real time. Display 430 displays superimposed image sequence for the user.

Superimposing processor 416 can add additional information to the super-imposed sequence, such as the location of the surgical tool, above or under the viewed plane. For example, portions of the surgical tool which are located on one side of the viewed plane shall be indicated using red color, portions of the surgical tool which are located on the other side of the viewed plane shall be indicated using blue color, and portions of the surgical tool which are located on viewed plane shall be indicated using red color.

It is noted that although two-dimensional system 400 provides less visual information than system 100 of FIG. 1, it requires significantly less processing power and storage area and hence can be manufactured at considerably lower costs.

It will be appreciated by persons skilled in the art that the present invention is not limited to what has been particularly shown and described hereinabove. Rather the scope of the present invention is defined only by the claims, which follow.

The invention claimed is:

1. Medical imaging and navigation system comprising:
a processor, connected to a display unit and to a database;
  a medical positioning system (MPS), connected to said processor, including a transducer MPS sensor and a surgical tool MPS sensor, said surgical tool MPS sensor being firmly attached to a surgical tool;
  a two-dimensional imaging system, connected to said processor, including an imaging transducer, said transducer MPS sensor being firmly attached to said imaging transducer;
  an inspected organ monitor interface, connected to said processor and to an organ monitor, said organ monitor monitoring an organ timing signal associated with an inspected organ;
  a superimposing processor, connected to said processor;
  wherein said processor receives: a plurality of two-dimensional images from said two-dimensional imaging system, acquired by said imaging transducer;
  the location and orientation of said imaging transducer from said medical positioning system, as detected by said transducer MPS sensor in a coordinate system, for each said two-dimensional images;
  said organ timing signal from said inspected organ monitor interface, as detected by said organ monitor, for each said two-dimensional images; and the location and orientation of said surgical tool, from said medical positioning system, as detected by said surgical tool MPS sensor in the coordinate system of the transducer MPS sensor;
  so that said location and orientation of said surgical tool and said location and orientation of said imaging transducer, are acquired in a single coordinate system, thereby eliminating computations for correlating said location and orientation of said transducer MPS sensor and said location and orientation of said surgical MPS sensor; and
  wherein for each said two-dimensional images, said processor stores said two-dimensional image in said database together with said location and orientation information of said imaging transducer, respective of said two-dimensional image and said organ timing signal, respective of said two-dimensional image, wherein said processor selects at least one of said stored two-dimensional images, having a stored organ timing signal substantially equal to a real time detected organ timing signal, wherein said superimposing processor superimposes a representation of said surgical tool on a visual representation of said selected two-dimensional images, and wherein said display presents the result of said superimposing.

2. The system according to claim 1, wherein said visual representation is a three-dimensional reconstructed image produced from said selected two-dimensional images, according to the location and orientation information of said imaging transducer associated with each said selected two-dimensional images.

3. The system according to claim 2, wherein a renderer renders said visual representation according to reference coordinates.

4. The system according to claim 3, wherein said reference coordinates are selected from the list consisting of: surgical tool coordinates; inspected organ coordinates; and coordinates of the body of the patient.

5. The system according to claim 4, wherein said visual representation is two-dimensional.

6. The system according to claim 5, wherein said representation of said surgical tool comprises a projection of a three-dimensional representation of said representation of said surgical tool, on said two-dimensional visual representation.

7. The system according to claim 1, wherein said representation of said surgical tool indicates an estimated location of said surgical tool.

8. The system according to claim 1, wherein said representation of said surgical tool indicates the orientation of said surgical tool.

9. The system according to claim 1, wherein portions of said surgical tool which are located above, below and within a viewed plane, are presented in different colors.

10. The system according to claim 1, wherein said representation of said surgical tool is in the form of a cursor.

11. The system according to claim 1, wherein said representation of said surgical tool is a pseudo realistic visualization of said surgical tool.

12. The system according to claim 1, wherein said visual representation is a three-dimensional reconstruction produced from said selected two-dimensional images, according to the location and orientation information of said imaging transducer associated with said selected two-dimensional images, discarding portions in said selected two-dimensional images which represent said surgical tool.

13. The system according to claim 1, wherein said medical positioning system further includes a goggles MPS sensor, wherein said display includes semi-transparent goggles, being attached to said goggles MPS sensor, and wherein said processor selects a viewing plane for said visual representation, according to the location and orientation information received from said goggles MPS sensor.

14. The system according to claim 13, wherein said location and orientation of said goggles MPS sensor is provided within said coordinate system.

15. The system according to claim 1, wherein said database is volumetric.

16. The system according to claim 1, wherein said display includes goggles.

17. The system according to claim 16, wherein said goggles are semi-transparent.

18. The system according to claim 1, wherein said two-dimensional imaging system is selected from the list consisting of:
ultra-sound;
inner-vascular ultra-sound;
X-ray;
Nuclear magnetic resonance;
Computerized tomography;
Position-emission tomography; and
Single-photon-emission tomography.

19. The system according to claim 1, wherein said surgical tool is selected from the list consisting of:
clamp;
laser cutter;
brush;
catheter;
stent;
balloon;
pace maker electrode;
solution dispensing unit;
neuron electrode;
substance collection unit;
surgical delivery tool;
gene delivery tool;
drug delivery tool; and
device delivery tool.

20. The system according to claim 1, wherein said medical positioning system further includes a body MPS sensor, for attaching to the body of the patient.

21. Medical imaging and navigation system comprising:
a processor, connected to a display unit and to a database;
a medical positioning system (MPS), connected to said processor, including a surgical tool MPS sensor being firmly attached to a surgical tool;
an inspected organ monitor interface, connected to said processor and to an organ monitor, said organ monitor monitoring an organ timing signal associated with an inspected organ; and
a superimposing processor, connected to said processor;
wherein said processor receives: said organ timing signal from said inspected organ monitor interface, as detected by said organ monitor; and the location and orientation of said surgical tool, from said medical positioning system, as detected by said surgical tool MPS sensor in a coordinate system;
wherein said processor selects images from said database, each said selected images having a stored organ timing signal substantially equal to a real-time detected organ timing signal, wherein said superimposing processor superimposes a representation of said surgical tool on said selected images, and wherein said display presents the result of said superimposing;
wherein said medical positioning system further includes a goggles MPS sensor, wherein said display includes semi-transparent goggles, being attached to said goggles MPS sensor, and wherein said processor selects a viewing plane for said visual representation, according to the location and orientation information received from said goggles MPS sensor;
so that said location and orientation information of said goggles MPS sensor is acquired within the coordinate system of said surgical tool MPS sensor, thereby eliminating computations for correlating said location and orientation of said goggles MPS sensor and said location and orientation of said surgical tool MPS sensor.

22. The system according to claim 21, wherein said selected images are three-dimensional.

23. The system according to claim 21, wherein said selected images are two-dimensional.

24. The system according to claim 21, wherein said representation of said surgical tool comprises a projection of a three-dimensional representation of said representation of said surgical tool, on said two-dimensional images.

25. The system according to claim 21, wherein said database is volumetric.

26. The system according to claim 21, wherein said database is further coupled to an image acquisition system.

27. The system according to claim 21, wherein said display includes goggles.

28. The system according to claim 21, wherein said goggles are semi-transparent.

29. The system according to claim 21, wherein said location and orientation information of said goggles MPS sensor is provided within the coordinate system of said selected images.

30. The system according to claim 21, wherein said two-dimensional imaging system is selected from the list consisting of:
- ultra-sound;
- inner-vascular ultra-sound;
- X-ray;
- Nuclear magnetic resonance;
- Computerized tomography;
- Position-emission tomography; and
- Single-photon-emission tomography.

31. The system according to claim 21, wherein said surgical tool is selected from the list consisting of:
- clamp;
- laser cutter;
- brush;
- catheter;
- stent;
- balloon;
- pace maker electrode;
- solution dispensing unit;
- neuron electrode;
- substance collection unit;
- surgical delivery tool;
- gene delivery tool;
- drug delivery tool; and
- device delivery tool.

32. The system according to claim 21, wherein said medical positioning system further includes a body MPS sensor, for attaching to the body of the patient.

33. Method for displaying an image sequence of a moving inspected organ, the method comprising the steps of:
- detecting an organ timing signal of said inspected organ, said organ timing signal defining an organ timing signal cycle;
- detecting a plurality of two-dimensional images of said inspected organ, using an image detector;
- detecting the location and orientation of said image detector;
- associating each of said two-dimensional images with said image detector location and orientation and with said detected organ timing signal;
- reconstructing a plurality of three-dimensional images from said two-dimensional images, each said three-dimensional images being reconstructed from two-dimensional images selected from said two-dimensional images, said selected two-dimensional images corresponding to a selected position within said organ timing signal cycle;
- selecting one of said three-dimensional images according to a real-time reading of said organ timing signal; and
- displaying said selected three-dimensional image;
- prior to said step of reconstructing: detecting the location and orientation of a surgical tool; and modifying at least one of said two-dimensional images, by discarding a portion of at least one of said two-dimensional images, said portion representing at least a portion of said surgical tool;
- detecting the location and orientation of a surgical tool; and modifying at least one of said two-dimensional images, by discarding a portion of at least one of said two-dimensional images, said portion representing at least a portion of said surgical tool;
- wherein said detected location and orientation of said surgical tool and said detected location and orientation of said image detector, are acquired in a single coordinate system, thereby eliminating computations for correlating said location and orientation of said transducer MPS sensor and said location and orientation of said surgical MPS sensor.

34. The method according to claim 33, further comprising the step of superimposing a representation of said surgical tool onto said selected three-dimensional image, prior to said step of displaying.

35. The method according to claim 34, wherein said representation of said surgical tool indicates an estimated an estimated location of said surgical tool.

36. The method according to claim 34, wherein said representation of said surgical tool indicates the orientation of said surgical tool.

37. The method according to claim 34, wherein portions of said surgical tool which are located above, below and within a viewed plane, are presented in different colors.

38. The method according to claim 34, wherein said representation of said surgical tool is in the form of a cursor.

39. The method according to claim 34, wherein said representation of said surgical tool is a pseudo relistic visualization of said surgical tool.

40. The method according to claim 34, wherein said representation of said surgical tool comprises a projection of a three-dimensional representation of said representation of said surgical tool, on each of said two-dimensional images.

41. The method according to claim 33, further comprising the following steps, prior to said step of displaying:
- detecting the location and orientation of a surgical tool; and
- superimposing a representation of said surgical tool onto said selected three-dimensional image, according to said detected location and orientation of said surgical tool.

42. The method according to claim 33, further comprising the following steps prior to said step of displaying:
- detecting the location and orientation of a surgical tool; and
- superimposing a representation of said detected location and orientation of said surgical tool, onto said selected three-dimensional image.

43. The method according to claim 33, further comprising, the following steps, after said step of selecting:
- detecting the location and orientation of a point of view of a user; and
- rendering said selected three-dimensional image according to said detected location and orientation of said point of view.

44. The method according to claim 43, further comprising the following steps prior to said step of rendering:

detecting the location and orientation a surgical tool; and
superimposing a representation of said surgical tool onto said selected three-dimensional image.

45. The method according to claim 43, further comprising the following steps, prior to said step of rendering:
  detecting the location and orientation of a surgical tool; and
  superimposing a representation of said detected location and orientation of said surgical tool onto said selected three-dimensional image.

46. The method according to claim 43, wherein said step of detecting said location and orientation of said point of view of said user, is performed using a location and orientation sensor attached to user worn goggles.

47. The method according to claim 46, wherein the information respective of said location and orientation sensor is provided with the coordinate system of a surgical tool.

48. The method according to claim 46, wherein the information respective of said location and orientation sensor is provided within the coordinate system of said inspected organ.

49. The method according to claim 46, wherein the information respective of said location and orientation sensor is provided within the coordinate system of the body of the patient.

50. The method according to claim 43, wherein said step of detecting said location and orientation of said point of view of said user, is performed using a location and orientation sensor attached to user worn semi-transparent goggles.

51. The method according to claim 33, wherein said surgical tool is selected from the list consisting of:
  clamp;
  laser cutter;
  brush;
  catheter;
  stent;
  balloon;
  pace maker electrode;
  solution dispensing unit;
  neuron electrode;
  substance collection unit;
  surgical delivery tool;
  gene delivery tool;
  drug delivery tool; and
  device delivery tool.

52. The method according to claim 33, further comprising the step of discarding portions in said selected two-dimensional images which represent a surgical tool, prior to said step of reconstructing.

53. The method according to claim 33, wherein said representation of said surgical tool comprises a projection of a three-dimensional representation of said representation of said surgical tool, on each of said two-dimensional images.

54. Method for displaying an image sequence of a moving inspected organ, the method comprising the steps of:
  detecting an organ timing signal of said inspected organ, said organ timing signal defining an organ timing signal cycle;
  selecting one of a previously stored three-dimensional images according to a real-time reading of said organ timing signal;
  detecting the location and orientation of a surgical tool;
  superimposing a representation of said surgical tool onto said selected three-dimensional image; and
  displaying said superimposed three-dimensional image;

further comprising the following steps prior to said step of selecting:
  detecting a plurality of two-dimensional images of said inspected organ, using an image detector;
  detecting the location and orientation of said image detector;
  associating each of said two-dimensional images with said location and orientation of said two-dimensional image and with a reading of said organ timing signal detected at the time of acquiring said two-dimensional image; and
  reconstructing a plurality of three-dimensional images from said two-dimensional images, each said three-dimensional images being reconstructed from two-dimensional images selected from said two-dimensional images, said selected two-dimensional images corresponding to a selected position within said organ timing signal cycle;
  wherein said detected location and orientation of said surgical tool and said detected location and orientation of said image detector, are acquired in a single coordinate system, thereby eliminating computations for correlating said detected location and orientation of said surgical tool and said detected location and orientation of said image detector.

55. The method according to claim 54, further comprising a step of modifying at least one of said two-dimensional images, by discarding a portion thereof which represents at least a portion of said surgical tool, wherein said step of modifying is performed following said step of associating, and following said step of detecting said surgical tool location and orientation.

56. The method according to claim 54, further comprising the following steps, before said step of displaying:
  detecting the location and orientation of a point of view of user; and
  rendering said selected three-dimensional image according to said detected location and orientation of said point of view.

57. The method according to claim 56, wherein said step of detecting said location and orientation of said point of view of said user, is performed using a location and orientation sensor attached to user worn goggles.

58. The method according to claim 57, wherein the information respective of said location and orientation sensor is provided within the coordinate system of said surgical tool.

59. The method according to claim 57, wherein the information respective of said location and orientation sensor is provided within the coordinate system of said inspected organ.

60. The method according to claim 57, wherein the information respective of said location and orientation sensor is provided within the coordinate system of the body of the patient.

61. The method according to claim 56, wherein said step of detecting said location and orientation of said point of view of said user, is performed using a location and orientation sensor attached to user worn semi-transparent goggles.

62. The method according to claim 54, wherein said surgical tool is selected from the list consisting of:
  clamp;
  laser cutter;
  brush;
  catheter;

stent;
balloon;
pace maker electrode;
solution dispensing unit;
neuron electrode;
substance collection unit;
surgical delivery tool;
gene delivery tool;
drug delivery tool; and
device delivery tool.

63. The method according to claim 54, wherein said representation of said surgical tool indicates an estimated location of said surgical tool.

64. The method according to claim 54, wherein said representation of said surgical tool indicates the orientation of said surgical tool.

65. The method according to claim 54, wherein portions of said surgical tool which are located above, below and within a viewed plane, are presented in different colors.

66. The method according to claim 54, wherein said representation of said surgical tool is in the form of a cursor.

67. The method according to claim 54, wherein said representation of said surgical tool is a pseudo realistic visualization of said surgical tool.

68. The method according to claim 54, wherein said step of reconstruction is performed according to the location and orientation information associated with each said selected two-dimensional images.

69. The method according to claim 54, further comprising the step of discarding portions in said selected two-dimensional images which represent said surgical tool, prior to said step of reconstructing.

70. The method according to claim 54, wherein said representation of said surgical tool comprises a projection of a three-dimensional representation of said representation of said surgical tool, on each of said two-dimensional images.

71. Method for displaying an image sequence of a moving inspected organ, the method comprising the steps of:
    detecting an organ timing signal of said inspected organ, said organ timing signal defining an organ timing signal cycle;
    detecting the location and orientation of a point of view of a user;
    selecting one of a previously stored three-dimensional images according to a real-time reading of said organ timing signal;
    rendering said selected three-dimensional image according to said detected location and orientation of said point of view; and
    displaying said selected three-dimensional image;
    further comprising the following steps prior to said step of selecting:
        detecting a plurality of two-dimensional images of said inspected organ, using an image detector;
        detecting the location and orientation of said image detector; associating each of said two-dimensional images with said location and orientation of said two-dimensional image and with a reading of said organ timing signal detected at the time of acquiring said two-dimensional image; and
        reconstructing a plurality of three-dimensional images from said two-dimensional images, each said three-dimensional images being reconstructed from two-dimensional images selected from said two-dimensional images, said selected two-dimensional images corresponding to a selected position within said organ timing signal cycle;
    further comprising the following steps prior to said step of reconstructing;
        detecting the location and orientation of a surgical tool; and
        modifying at least one of said two-dimensional images, by discarding a portion of at least one of said two-dimensional images, said portion representing at least a portion of said surgical tool;
        wherein said detected location and orientation of said surgical tool and said detected location and orientation of said image detector, are acquired in a single coordinate system, thereby eliminating computations for correlating said detected location and orientation of said surgical tool and said detected location and orientation of said image detector.

72. The method according to claim 71, further comprising the step of superimposing a representation of said surgical tool onto said selected three-dimensional image, prior to said step of displaying.

73. The method according to claim 72, wherein said representation of said surgical tool indicates an estimated location of said surgical tool.

74. The method according to claim 72, wherein said representation of said surgical tool indicates the orientation of said surgical tool.

75. The method according to claim 72, wherein portions of said surgical tool which are located above, below and within a viewed plane, are presented in different colors.

76. The method according to claim 72, wherein said representation of said surgical tool is in the form of a cursor.

77. The method according to claim 72, wherein said representation of said surgical tool is a pseudo realistic visualization of said surgical tool.

78. The method according to claim 72, wherein said representation of said surgical tool comprises a projection of a three-dimensional representation of said representation of said surgical tool, on each of said two-dimensional images.

79. The method according to claim 71, further comprising the following steps, after said step of associating:
    detecting the location and orientation of a surgical tool;
    modifying at least one of said two-dimensional images, by discarding a portion of at least one of said two-dimensional images, which represents said surgical tool; and
    superimposing a representation of said surgical tool onto said selected three-dimensional image.

80. The method according to claim 71, wherein said step of detecting said location and orientation of said point of view of said user, is performed using a location and orientation sensor attached to user worn goggles.

81. The method according to claim 80, wherein the information respective of said location and orientation sensor is provided within the coordinate system of a surgical tool.

82. The method according to claim 80, wherein the information respective of said location and orientation sensor is provided within the coordinate system of said inspected organ.

83. The method according to claim 80, wherein the information respective of said location and orientation sensor is provided within the coordinate system of the body of the patient.

84. The method according to claim 71, wherein said step of detecting said location and orientation of said point of view of said user, is performed using a location and orientation sensor attached to user worn semi-transparent goggles.

85. The method according to claim 71, wherein said surgical tool is selected from the list consisting of:
   clamp;
   laser cutter;
   brush;
   catheter;
   stent;
   balloon;
   peace maker electrode;
   solution dispensing unit;
   neuron electrode;
   substance collection unit;
   surgical delivery tool;
   gene delivery tool;
   drug delivery tool; and
   device delivery tool.

86. The method according to claim 71, further comprising the step of discarding portions in said selected two-dimensional images which represent a surgical tool, prior to said step of reconstructing.

87. Method for displaying an image sequence of a moving inspected organ, each image in said image sequence being associated with the location and orientation thereof within a predetermined coordinate system, the method comprising the steps of:
   detecting an organ timing signal of said inspected organ;
   selecting one of a previously stored two-dimensional images according to a real-time reading of said organ timing signal; and
   displaying said selected two-dimensional image;
   further comprising the following steps, before said step of displaying:
      detecting the location and orientation of a surgical tool; and
      projecting a representation of said surgical tool onto said selected two-dimensional image;
      wherein said detected location and orientation of said surgical tool and said detected location and orientation of said image detector, are acquired in a single coordinate system, thereby eliminating computations for correlating said detected location and orientation of said surgical tool and said detected location and orientation of said image detector.

88. The method according to claim 87, further comprising the preliminary steps of:
   detecting a plurality of two-dimensional images of said inspected organ, using an image detector; and
   detecting the location and orientation of said image detector for each said two-dimensional images.

89. The method according to claim 87, further comprising the preliminary step of storing said two-dimensional images and the respective said detected locations and orientations of said image detector, in a database.

90. The method according to claim 87, further comprising the preliminary steps of:
   determining if at least one of said two-dimensional images deviates from a selected plane; and
   reporting said deviation.

91. The method according to claim 87, further comprising the step of detecting the location and orientation of a point of view of a user, before said step of displaying, wherein said stored two-dimensional image is selected according to said detected location and orientation of said point of view.

92. The method according to claim 91, further comprising the preliminary steps of:
   detecting a plurality of two-dimensional images of said inspected organ, using an image detector;
   detecting the location and orientation of said image detector, respective of each of said two-dimensional images; and
   storing said two-dimensional images and the respective said detected locations and orientations of said image detector, in a database.

93. The method according to claim 91, wherein said step of detecting said location and orientation of said point of view of said user, is performed using a location and orientation sensor attached to user worn goggles.

94. The method according to claim 87, wherein the information respective of said location and orientation sensor is provided within the coordinate system of a surgical tool.

95. The method according to claim 87, wherein the information respective of said location and orientation sensor is provided within the coordinate system of said inspected organ.

96. The method according to claim 87, wherein the information respective of said location and orientation sensor is provided within the coordinate system of the body of the patient.

97. The method according to claim 87, wherein said surgical tool is selected from the list consisting of:
   clamp;
   laser cutter;
   brush;
   catheter;
   stent;
   balloon;
   pace maker electrode;
   solution dispensing unit;
   neuron electrode;
   substance collection unit;
   surgical delivery tool;
   gene delivery tool;
   drug delivery tool; and
   device delivery tool.

98. The method according to claim 87, wherein said representation of said surgical tool indicates an estimated location of said surgical tool.

99. The method according to claim 87, wherein said representation of said surgical tool indicates the orientation of said surgical tool.

100. The method according to claim 87, wherein portions of said surgical tool which are located above, below and within said selected two-dimensional image, are presented in different colors.

101. The method according to claim 87, wherein said representation of said surgical tool is in the form of cursor.

102. The method according to claim 87, wherein said representation of said surgical tool is a pseudo realistic visualization of said surgical tool.

* * * * *